United States Patent
Berti et al.

(10) Patent No.: US 9,439,955 B2
(45) Date of Patent: *Sep. 13, 2016

(54) CONJUGATED β-1,3-LINKED GLUCANS

(71) Applicant: Novartis AG, Basel (CH)

(72) Inventors: Francesco Berti, Siena (IT); Paolo Costantino, Siena (IT); Maria Rosaria Romano, Siena (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/928,070

(22) Filed: Jun. 26, 2013

(65) Prior Publication Data

US 2013/0315960 A1    Nov. 28, 2013

Related U.S. Application Data

(62) Division of application No. 12/734,795, filed as application No. PCT/IB2008/003680 on Nov. 26, 2008.

(60) Provisional application No. 61/004,333, filed on Nov. 26, 2007.

(51) Int. Cl.
| | |
|---|---|
| *A61K 39/00* | (2006.01) |
| *A61K 47/48* | (2006.01) |
| *A61K 39/385* | (2006.01) |
| *A61K 31/716* | (2006.01) |
| *A61P 37/02* | (2006.01) |
| *C08B 37/00* | (2006.01) |
| *C07K 14/195* | (2006.01) |
| *A61K 9/00* | (2006.01) |
| *A61K 9/02* | (2006.01) |
| *A61K 9/107* | (2006.01) |

(52) U.S. Cl.
CPC ......... *A61K 39/0002* (2013.01); *A61K 31/716* (2013.01); *A61K 47/4823* (2013.01); *A61K 47/4833* (2013.01); *A61K 47/48261* (2013.01); *A61K 9/0019* (2013.01); *A61K 9/02* (2013.01); *A61K 9/107* (2013.01); *A61K 2039/55505* (2013.01); *A61K 2039/55561* (2013.01); *A61K 2039/55566* (2013.01); *A61K 2039/6037* (2013.01)

(58) Field of Classification Search
None
See application file for complete search history.

(56) References Cited

U.S. PATENT DOCUMENTS

| | | |
|---|---|---|
| 4,659,569 A | 4/1987 | Mitsuhashi et al. |
| 2004/0127458 A1 | 7/2004 | Hunter |
| 2005/0208079 A1 | 9/2005 | Cassone et al. |
| 2010/0266626 A1 | 10/2010 | Berti et al. |
| 2011/0045015 A1 | 2/2011 | Berti et al. |

FOREIGN PATENT DOCUMENTS

| | | |
|---|---|---|
| EP | 0 640 348 | 3/1995 |
| JP | 02-218615 | 8/1990 |
| JP | 03 227939 | 10/1991 |
| JP | 04 346931 | 12/1992 |
| JP | 06 065303 | 3/1994 |
| JP | 06-172217 | 6/1994 |
| JP | 06 172217 | 6/1994 |
| JP | 2007/2289748 | 11/1995 |
| JP | 10 194976 | 7/1998 |
| JP | 10 194977 | 7/1998 |
| JP | 2005-535298 | 11/2005 |
| WO | WO 95/30022 | 11/1995 |
| WO | WO 96/14873 | 5/1996 |
| WO | WO 03/097091 | 11/2003 |
| WO | WO 2004/100965 | 11/2004 |
| WO | WO 2004/105775 | 12/2004 |
| WO | WO 2005/027936 | 3/2005 |
| WO | WO 2009/068996 | 6/2009 |
| WO | WO 2009/077854 | 6/2009 |
| WO | WO 2012/103058 | 8/2012 |

OTHER PUBLICATIONS

The New Riverside University Dictionary, 1984, p. 933.*
Illustrated Stedman's Medical Dictionary, 24th Edition, Williams and Wilkins, London, p. 707, 1982.*
Nollstadt et al. Antimicrob. Agents Chemother. 38: 2258-65, 1994.*
Perera et al. Antimicrob. Agents Chemother. 46: 1695-1703, 2002.*
Lin et al. J. Clin. Microbiol. 33: 1815-1821, 1995.*
McCullough et al. J. Clin. Microbiol. 33: 696-700, 1995.*
Mathaba et al. J. Gastreoenterol. Hepatol. 15: 53-60, 2000.*
Cutler et al. Nature Rev. Immunol. 5, 13-28, Jan. 2007.*
Kageyama et al. J. Biochem. 142: 95-104, published online May 24, 2007.*
Casadevall et al., "Polysaccharide-containing conjugate vaccines for fungal diseases," Trends in Molecular Medicine, Elsevier Current Trends, vol. 12, No. 1, pp. 6-9 (2006).
Fan et al., "Improving functional properties of soy protein hydrolysate by conjugation with curdlan," J. Food Sci., 71(5):C285-C291 (2006).
Honey et al., "β-glucan conjugate provides protection," Nat. Rev. Immunol. 5(10):746-747 (2005).
Ohya et al., "Design of d-glucose analogue of MDP/CM-curdlan conjugate and its immunological enhancement activity," Carb. Poly., Applied Science Pub, Ltd., Barking, GB, 20(1):43-49 (1993).
Ohya et al., "Immunological enhancement activity of muramyl dipeptide analogue/CM-curdlan conjugate," Carbohydrate Poly., Applied Science Pub, Ltd., Barking, GB, 23(1):47-54 (1994).
Raa et al., "The use of immune-stimulants in fish and shellfish feeds," Avances Ennutricion Acuicola V. Memorias Del Simposium Internacional de Nutrition Acuicola, XX, XX, pp. 47-56 (2000).

(Continued)

*Primary Examiner* — S. Devi
(74) *Attorney, Agent, or Firm* — Robert L. Robins; Robins Law Group

(57) ABSTRACT

Glucans having exclusively or mainly β-1,3 linkages are used as immunogens. These comprise β-1,3-linked glucose residues. Optionally, they may include β-1,6-linked glucose residues, provided that the ratio of β-1,3-linked residues to β-1,6-linked residues is at least 8:1 and/or there are one or more sequences of at least five adjacent non-terminal residues linked to other residues only by β-1,3 linkages. The glucans will usually be used in conjugated form. A preferred glucan source is curdlan, which may be hydrolyzed to a suitable form prior to conjugation.

14 Claims, 10 Drawing Sheets

(56) References Cited

OTHER PUBLICATIONS

Sengupta et al., "Conjugation of β-1,3-D-glucan to microbeads potentiates the stimulation of interleukin-1 secretion and survival from *Escherichia coli* infection in mice," S.T.P. Pharma Sciences 199903 FR, 9(2):197-202 (1999).

Torosantucci et al., "A novel glycol-conjugate vaccine against fungal pathogens," J. Exp. Med. 202(5):597-606 (2005).

Bromuro et al., "Beta-glucan-CRM 197 conjugates as candidates antifungal vaccines," Vaccine, 28:2615-2623 (2010).

Selvaraj et al., "Adjuvant and immunostimulatory effects of beta-glucan administration in combination with lipopolysaccharide enhances survival and some immune parameters in carp challenged with Aeromonas hydrophila," Veterinary Immunology and Immunopathology, Amsterdam, NL, 114(1-2):15-24 (2006).

Schellack et al., Vaccine, 24:5461-5472 (2006).

SIGMA Chemical Catalog, p. 583 (2003).

Petersen et al., "A transglycosylating 1,3(4)-β-glucanase from *Rhodothermus marinus* NMR analysis of enzyme reactions," Eur. J. Biochem., 267:361-369 (2000).

Japanese Examination Report, Japanese Patent Application No. 2010-534565, Mailing Date May 13, 2013.

Torosantucci et al., "A Novel Glyco-Conjugate Vaccine Against Fungal Pathogens", The Journal of Experimental Medicine, 202(5):597-606 (2005).

Jamois et al., "Glucan-Like Synthetic Oligosaccharides: Iterative Synthesis of Linear Oligo-β-(1,3)-Glucans and Immunostimulatory Effects", Glycobiology, 15(4):393-407 (2005).

Ashida et al., "Oral Administration of Curdlan (β-1,3-Glucan) Potentiates the Non-Specific Immune System of Japanese Flounder, Paralichthys Olivaceus, and It's Effect Is Influenced by the Feeding Period," Suisanzoshoku, 47(3):439-444 (1999).

Sasaki et al., "Dependence of Chain Length of Antitumor Activity of (1→3)-β-D-Glucan From *Alcaligenes faecalls* Var. *myxogenes*, IFO 13140, and It's Acid-Degraded Products," Cancer Research, 38:379-383 (1978).

Oya et al., 66$^{th}$ Fall Meeting (with Union Debate) Conference of the Union of Chemistry-Related Societies Research Presentation, Joint Meeting, Proceeding of Lecture, p. 306, 3C418, 1993 (in Japanese with English translation).

Kanke et al., Drug Delivery System, 7(2):135-140 (1992).

Oya et al., 66$^{th}$ Fall Meeting (with Union Debate) Conference of the Union of Chemistry-Related Societies Research Presentation, Joint Meeting, Proceeding of Lecture, p. 306, 3C418 (1993).

McIntosh et al., "Curdlan and Other Bacterial (1-3)-β-D-Glucans," Appl. Microbiol Biotechnol, 68:163-173 (2005).

Sigma Chemical Catalog, 2002-2003, p. 1216.

\* cited by examiner

*Figure 1*
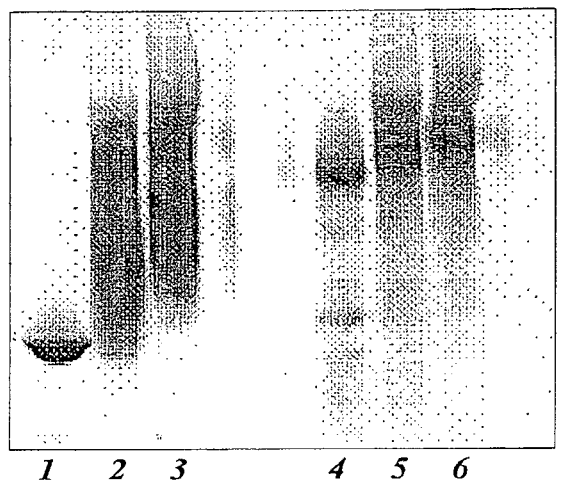
*Figure 2*
*Figure 2A*
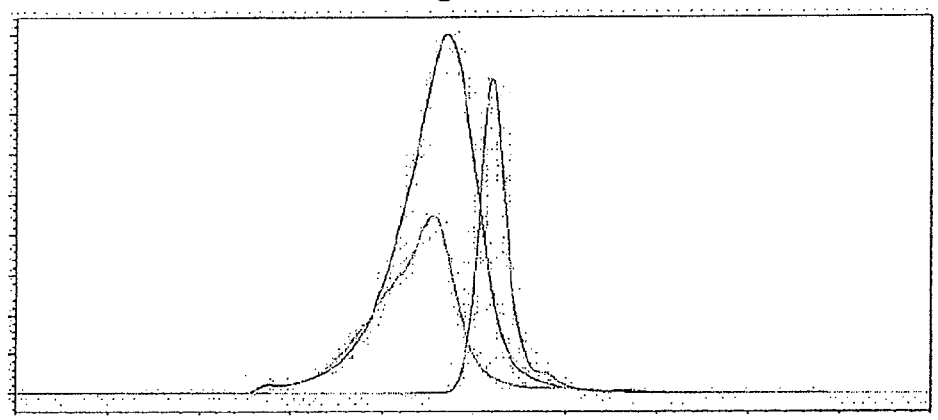
*Figure 2B*
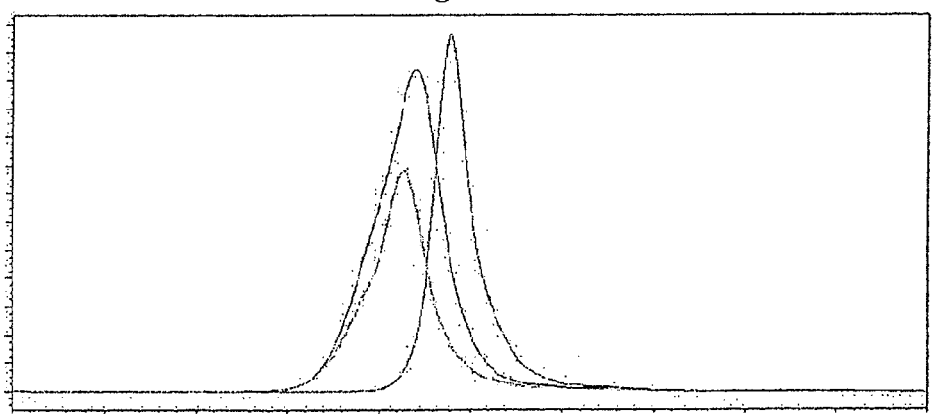

A

B

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(26)
<223> OTHER INFORMATION: "nn" from 1 through 26 represents 13 repeats of
      deoxy-inosinic-deoxy-cytidylic acid
<220> FEATURE:
<221> NAME/KEY: variation
<222> LOCATION: (1)..(26)
<223> OTHER INFORMATION: nn

```
<400> SEQUENCE: 1
nnnnnnnnnn nnnnnnnnnn nnnnnn                                    26

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Lys Leu Lys Leu Leu Leu Leu Leu Lys Leu Lys
1               5                   10
```

US 9,439,955 B2

CONJUGATED β-1,3-LINKED GLUCANS

CROSS REFERENCE TO RELATED APPLICATIONS

This application is a divisional application of U.S. patent application Ser. No. 12/734,795, filed May 25, 2010, which is a §371 filing from PCT/IB2008/003680, filed Nov. 26, 2008, and claims the benefit under 35 U.S.C. §119(e)(1) of U.S. Provisional Application Ser. No. 61/004,333, filed on 26 Nov. 2007, which applications are incorporated herein by reference in their entireties and from which applications priority is claimed pursuant to the provisions of 35 U.S.C. §§119/120.

TECHNICAL FIELD

The invention relates to vaccines, more particularly those against fungal infections and disease.

BACKGROUND OF THE INVENTION

Fungal infections are prevalent in several clinical settings, particularly in immunocompromised patients. The emergence of resistance to antimycotics, in particular to the azoles, has increased interest in therapeutic and prophylactic vaccination against these fungi [1]. Among fungal pathogens, *Candida albicans* is one of the most prevelent. This organism is one of the principal agents of widespread opportunistic infections in humans and causes candidiasis, a condition which is found in both normal and immunocompromised patients. There have been several attempts to provide anti-*Candida* vaccines.

Glucans are glucose-containing polysaccharides found inter alia in fungal cell walls. α-glucans include one or more α-linkages between glucose subunits and β-glucans include one or more β-linkages between glucose subunits. Within a typical fungal cell wall, β-1,3-glucan microfibrils are interwoven and crosslinked with chitin microfibrils to form the inner skeletal layer, whereas the outer layer consists of β-1,6-glucan and mannoproteins, linked to the inner layer via chitin and β-1,3-glucan.

In *C. albicans*, 50-70% of the cell wall is composed of β-1,3- and β-1,6-glucans. The use of β-glucans as antifungal vaccines is reviewed in reference 2. Protective antibodies against *C. albicans* β-1,6-glucan have been generated in mice [3,4]. Mice in which anti β-1,6-glucan antibodies were raised by vaccination with mannoprotein-depleted *C. albicans* cells were shown to have some protection against systemic challenge by *C. albicans*. Furthermore, mice passively immunised with these anti β-1,6-glucan antibodies demonstrated a raised level of protection against *C. albicans*. Similarly, anti-β-1,3-glucan antibodies have been found to be protective against *C. albicans*, and monoclonal antibodies that bind to β-1,3-glucans could protect against disseminated experimental cadidiasis [5].

It is an object of the invention to provide further and better glucan antigens for inducing protective and/or therapeutic immune responses against infections, particularly against fungal infections.

SUMMARY OF THE INVENTION

The present invention relates to glucans for use in medicine. The glucans of the invention can either (i) have exclusively β-1,3-linked glucose residues or (ii) comprise both β-1,3-linked and β-1,6-linked glucose residues, provided that the ratio of β-1,3-linked residues to β-1,6-linked residues is at least 8:1 and/or there are one or more sequences of at least five adjacent non-terminal residues linked to other residues only by β-1,3 linkages. In particular, the glucans may either (i) have exclusively β-1,3-linked glucose residues or (ii) comprise both β-1,3-linked and β-1,6-linked glucose residues, provided that the ratio of β-1,3-linked residues to β-1,6-linked residues is at least 8:1. In one embodiment, the glucan is linear β-D-glucopyranose with exclusively 1,3 linkages. The glucan can be a curdlan, a paramylon, or a fragment thereof. The glucan can be a hydrolysis fragment of curdlan. In certain embodiments, the glucan has from 2-60 glucose monosaccharide units. The glucan may be for use as an immunogen. In particular, the glucan may be for use in providing a protective antibody response, e.g. against *C. albicans*.

The present invention also relates to conjugates comprising a glucan of the invention linked to a carrier molecule. The carrier molecule can be a bacterial toxin or non-toxic derivative thereof. In a particular embodiment, the carrier is CRM197.

The present invention also relates to pharmaceutical compositions comprising a glucan or conjugate of the invention in combination with a pharmaceutically acceptable carrier.

The present invention further relates to methods for raising an immune response in a mammal, comprising administering a glucan, conjugate or pharmaceutical composition of the invention to the mammal.

BRIEF DESCRIPTION OF DRAWINGS

FIG. 1 shows SDS-PAGE of saccharides and conjugates. Lanes are: (1) CRM197; (2) laminarin conjugated to CRM197; (3) hydrolysed curdlan conjugated to CRA/1197; (4) tetanus toxoid monomer, Tt; (5) laminarin conjugated to Tt; (6) hydrolysed curdlan conjugated to Tt.

FIG. 2 shows SEC-HPLC profiles for conjugates. FIG. 2A shows profiles for CRM197 conjugates, and FIG. 2B shows profiles for Tt conjugates. The right-most peak in both cases is the profile of unconjugated carrier. The lowest peak is a curdlan conjugate. The third peak is a laminarin conjugate.

DETAILED DESCRIPTION OF THE INVENTION

Figure 3:
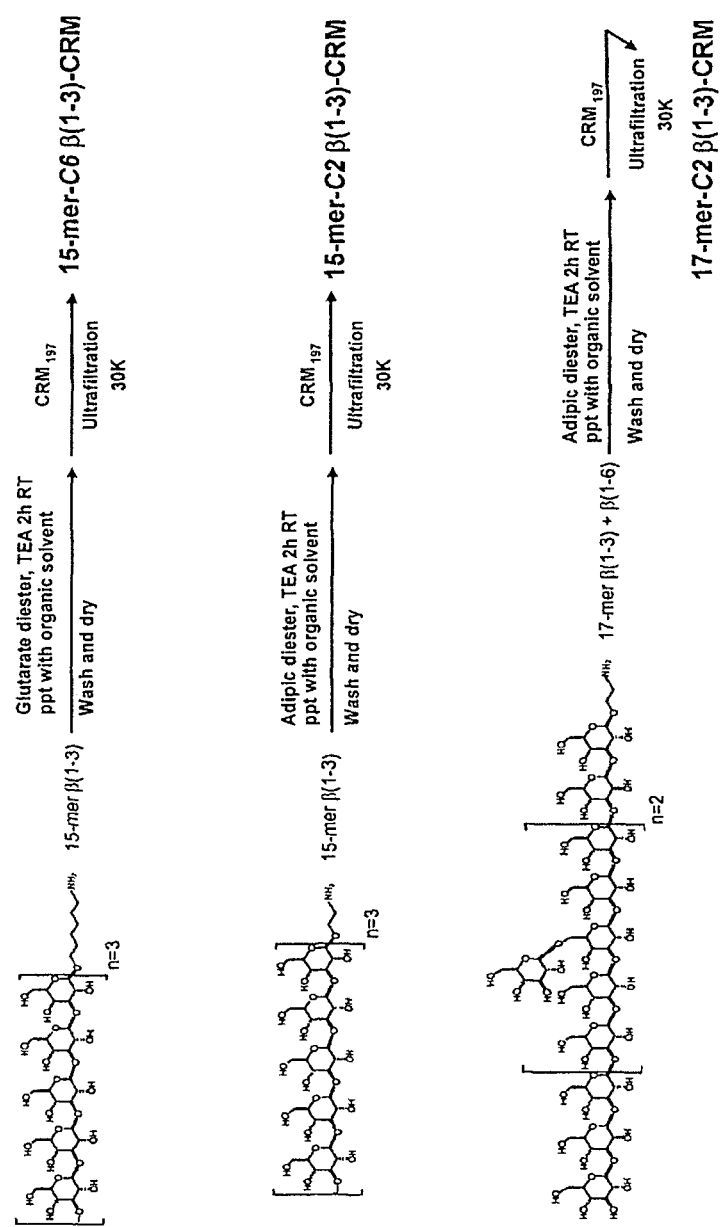
FIG. 3 summarises the conjugation of synthetic glucans.

Commercially available β-glucans used in references 3 and 5 were laminarin and pustulan. Laminarins are found in brown algae and seaweeds and are β-1,3 glucans with some β-1,6 branching. The β(1-3):β(1-6) ratio varies between different sources e.g. it is as low as 3:2 in *Eisenia bicyclis* laminarin, but as high as 7:1 in *Laminaria digititata* laminarin [6]. Pustulan is a non-fungal linear β-1,6-linked glucan from *Umbilicaria papullosa*. Other glucans, such as scleroglucan (*Sclerotinia sclerotiorum*) and schizophyllan, have a β-1,3):β(1-6) ratio of 3:1 (see Table 2 of ref. 7). Other natural mixed β-glucans include lentinan and sonifilan.

According to the invention, glucans having exclusively or mainly β-1,3 linkages are used as immunogens. The inventors have found that these glucans may be more immunogenic than glucans comprising other linkages, particularly glucans comprising β-1,3 linkages and a greater proportion of β-1,6 linkages. The glucans of the invention comprise β-1,3-linked glucose residues. Optionally, they may include β-1,6-linked glucose residues, provided that the ratio of β-1,3-linked residues to β-1,6-linked residues is at least 8:1 and/or there are one or more sequences of at least five adjacent non-terminal residues linked to other residues only by β-1,3 linkages. The inventors have found that the presence of five adjacent non-terminal residues linked to other residues only by β-1,3 linkages may provide a protective antibody response, e.g. against *C. albicans*. The glucans will usually be used in conjugated form.

Thus the invention provides a glucan for use in medicine, wherein the glucan either (i) has exclusively β-1,3-linked glucose residues or (ii) comprises both β-1,3-linked and β-1,6-linked glucose residues, provided that the ratio of β-1,3-linked residues to β-1,6-linked residues is at least 8:1 and/or there are one or more sequences of at least five adjacent non-terminal residues linked to other residues only by β-1,3 linkages. In a particular embodiment, the invention therefore provides a glucan for use in medicine, wherein the glucan either (i) has exclusively β-1,3-linked glucose residues or (ii) comprises both β-1,3-linked and β-1,6-linked glucose residues, provided that the ratio of β-1,3-linked residues to β-1,6-linked residues is at least 8:1.

The invention also provides a conjugate comprising a glucan linked to a carrier molecule, wherein the glucan either (i) has exclusively β-1,3-linked glucose residues or (ii) comprises both β-1,3-linked and β-1,6-linked glucose residues, provided that the ratio of β-1,3-linked residues to β-1,6-linked residues is at least 8:1 and/or there are one or more sequences of at least five adjacent non-terminal residues linked to other residues only by β-1,3 linkages. In a particular embodiment, the invention therefore provides a conjugate comprising a glucan linked to a carrier molecule, wherein the glucan either (i) has exclusively β-1,3-linked glucose residues or (ii) comprises both β-1,3-linked and β-1,6-linked glucose residues, provided that the ratio of β-1,3-linked residues to β-1,6-linked residues is at least 8:1.

Preferred glucans are linear β-D-glucopyranoses with exclusively 1,3 linkages.

The Glucan

The invention uses glucans having exclusively or mainly β-1,3 linkages between D-glucose residues. They are preferably linear.

Thus the glucan may be made solely of β-1,3-linked glucose residues. Optionally, though, it may include monosaccharide residues that are not β-1,3-linked glucose residues (e.g. it may include β-1,6-linked glucose residues), provided that the ratio of β-1,3-linked glucose residues to these other residues is at least 8:1 (e.g. ≥9:1, ≥10:1, ≥11:1, ≥12:1, ≥13:1, ≥14:1, ≥15:1, ≥16:1, ≥17:1, ≥18:1, ≥19:1, ≥20:1, ≥25:1, ≥30:1, ≥35:1, ≥40:1, ≥45:1, ≥50:1, ≥75:1, ≥100:1, etc.) and/or there are one or more (e.g. ≥1, ≥2, ≥3, ≥4, ≥5, ≥6, ≥7, ≥8, ≥9, ≥10, ≥11, ≥12, etc.) sequences of at least five (e.g. ≥5, ≥6, ≥7, ≥8, ≥9, ≥10, ≥11, ≥12, ≥13, ≥14, ≥15, ≥16, ≥17, ≥18, ≥19, ≥20, ≥30, ≥40, ≥50, ≥60, etc.) adjacent non-terminal residues linked to other residues only by β-1,3 linkages. By "non-terminal" it is meant that the residue is not present at a free end of the glucan. In some embodiments, the adjacent non-terminal residues may not include any residues coupled to a carrier molecule, linker or spacer as described below.

In contrast, the ratio of β-1,3-linked glucose to β-1,6 linked glucose in a laminarin from *L. digitata* is 7:1, as its repeating structure is as follows:

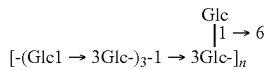

A mixed β-1,3/β-1,6 glucan with the specified ratio and/or sequence may be found in nature, or it may be made artificially. For instance, it may be made by chemical synthesis, in whole or in part. Methods for the chemical synthesis of β-1,3/β-1,6 glucans are well known in the art, for example from references 8-18. Mixed β-1,3/β-1,6 glucans with the specified ratio and optional sequence may also be made starting from *L. digitata* laminarin shown above (having a 7:1 ratio) by treating it with a β-1,6-glucanase (also known as glucan endo-1,6-β-glucosidase, 1,6-β-D-glucan glucanohydrolase, etc.; EC 3.2.1.75) until a desired ratio and/or sequence is reached.

When a glucan containing solely β-1,3-linked glucose is desired, this process may be pursued to completion, as β-1,6-glucanase will eventually yield pure β-1,3 glucan. More conveniently, however, a pure β-1,3-glucan may be used. These may be made synthetically, by chemical and/or enzymatic synthesis e.g. using a (1→3)-β-D-glucan synthase, of which several are known from many organisms (including bacteria, yeasts, plants and fungi). Methods for the chemical synthesis of β-1,3 glucans are well known in the art, for example from references 19-22. As a useful alternative to synthesis, a natural β-1,3-glucan may be used, such as a curdlan (linear β-1,3-glucan from an *Agrobacterium* previously known as *Alcaligenes faecalis* var. *myxogenes*; commercially available e.g. from Sigma-Aldrich catalog C7821) or paramylon β-1,3-glucan from *Euglena*).

Organisms producing high levels of β-1,3-glucans are known in the art e.g. the *Agrobacterium* of refs. 23 & 24, or the *Euglena gracilis* of ref. 25.

A preferred source of β-1,3-linked glucans for use with the invention is curdlan. Curdlan is typically obtained with a molecular weight of at least 100 kDa and a DP (degree of polymerisation) of at least about 450 units. It forms a parallel in-phase triple right-handed six-fold helix that is insoluble in water. In its natural form, therefore, curdlan is not well suited to immunisation. Thus the invention may use a curdlan hydrolysate. Acid hydrolysis of curdlan can break its backbone to reduce its average molecular weight such that it becomes soluble and is amenable to chemical and physical manipulation. Ideally, the invention uses a curdlan hydrolysate having an average molecular weight in the ranges given below. Rather than use hydrolysis, enzymatic digestion can be used e.g. with a glucanase, such as a β-1,3-glucanase. Digestion may proceed until the curdlan has an average molecular weight in the ranges given below.

Whereas natural curdlans have very high molecular weights, the glucans used with the invention have lower molecular weights in order to improve solubility in aqueous media, particularly those containing 60 or fewer monosaccharide units (e.g. 59, 58, 57, 56, 55, 54, 53, 52, 51, 50, 49, 48, 47, 46, 45, 44, 43, 42, 41, 40 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4). A glucan having a number of glucose monosaccharides in the range of 2-60 may be used e.g. between 10-50 or between 20-40 glucose units. A glucan with 25-30 glucose monosaccharide units is particularly useful. A glucan with 11-19, e.g. 13-17 and particularly 15, glucose monosaccharide units is also useful. Accordingly, a glucan with the following structure is specifically envisaged for use in the present invention:

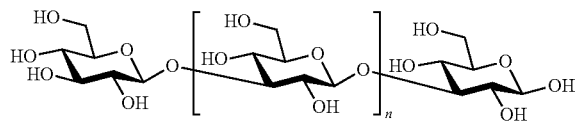

wherein n+2 is in the range of 2-60, e.g. between 10-50 or between 20-40. Preferably, n+2 is in the range of 25-30 or 11-19, e.g. 13-17. The inventors have found that n+2=15 is suitable.

The glucan having exclusively or mainly β-1,3 linkages (as defined above) is preferably a single molecular species. In this embodiment, all of the glucan molecules are identical in terms of sequence. Accordingly, all of the glucan molecules are identical in terms of their structural properties, including molecular weight etc. Typically, this form of glucan is obtained by chemical synthesis, e.g. using the methods described above. For example, reference 20 describes the synthesis of a single β-1,3 linked species. Alternatively, in other embodiments, the glucan may be obtained from a natural glucan, e.g. a glucan from *L. digitata*, *Agrobacterium* or *Euglena* as described above, with the glucan being purified until the required single molecular species is obtained. Natural glucans that have been purified in this way are commercially available. A glucan that is a single molecular species may be identified by measuring the polydispersity (Mw/Mn) of the glucan sample. This parameter can conveniently be measured by SEC-MALLS, for example as described in reference 26. Suitable glucans for use in this embodiment of the invention have a polydispersity of about 1, e.g. 1.01 or less. The inventors have found that glucans that are single molecular species may be more immunogenic than more polydisperse glucans, particularly when used in a composition that further includes an adjuvant.

Solubility of curdlan can be increased by introducing ionic groups (e.g. by sulfation, particularly at O-6). Such modifications may be used with the invention, but are ideally avoided as they may alter the molecule's antigenicity.

In addition to including a glucan having exclusively or mainly β-1,3 linkages (as defined above), a composition of the invention may include a second glucan, wherein the second glucan can have a ratio of β-1,3-linked glucose residues to β-1,6-linked glucose residues of 7:1 or less. For instance, a composition may include both a laminarin glucan and a curdlan glucan.

Conjugates

Pure β-glucans are poor immunogens. For protective efficacy, therefore, β-glucans may be presented to the immune system as a glucan-carrier conjugate. The use of conjugation to carrier proteins in order to enhance the immunogenicity of carbohydrate antigens is well known [e.g. reviewed in refs. 27 to 35 etc.] and is used in particular for pediatric vaccines [36].

The invention provides a conjugate of (i) a glucan, as defined above, and (ii) a carrier molecule.

The carrier molecule may be covalently conjugated to the glucan directly or via a linker. Any suitable conjugation reaction can be used, with any suitable linker where desired.

Attachment of the glucan antigen to the carrier is preferably via a —NH$_2$ group e.g. in the side chain of a lysine residue in a carrier protein, or of an arginine residue. Where a glucan has a free aldehyde group then this can react with an amine in the carrier to form a conjugate by reductive amination. Attachment to the carrier may also be via a —SH group e.g. in the side chain of a cysteine residue. Alternatively the glucan antigen may be attached to the carrier via a linker molecule.

The glucan will typically be activated or functionalised prior to conjugation. Activation may involve, for example, cyanylating reagents such as CDAP (e.g. 1-cyano-4-dimethylamino pyridinium tetrafluoroborate [37, 38, etc.]). Other suitable techniques use carbodiimides, hydrazides, active esters, norborane, p-nitrobenzoic acid, N-hydroxysuccinimide, S—NHS, EDC, TSTU (see also the introduction to reference 33).

Direct linkages to the protein may comprise oxidation of the glucan followed by reductive amination with the protein, as described in, for example, references 39 and 40.

Linkages via a linker group may be made using any known procedure, for example, the procedures described in references 41 and 42. Typically, the linker is attached via the anomeric carbon of the glucan. A preferred type of linkage is an adipic acid linker, which may be formed by coupling a free —NH$_2$ group (e.g. introduced to a glucan by amination) with adipic acid (using, for example, diimide activation), and then coupling a protein to the resulting saccharide-adipic acid intermediate [31, 43, 44].

A similar preferred type of linkage is a glutaric acid linker, which may be formed by coupling a free —NH$_2$ group with glutaric acid in the same way. Adipid and glutaric acid linkers may also be formed by direct coupling to the glucan, i.e. without prior introduction of a free group, e.g. a free —NH$_2$ group, to the glucan, followed by coupling a protein to the resulting saccharide-adipic/glutaric acid intermediate. Another preferred type of linkage is a carbonyl linker, which may be formed by reaction of a free hydroxyl group of a modified glucan with CDI [45, 46] followed by reaction with a protein to form a carbamate linkage. Other linkers include β-propionamido [47], nitrophenyl-ethylamine [48], haloacyl halides [49], glycosidic linkages [50], 6-aminocaproic acid [51], N-succinimidyl-3-(2-pyridyldithio)-propionate (SPDP) [52], adipic acid dihydrazide ADH [53], $C_4$ to $C_{12}$ moieties [54], etc. Carbodiimide condensation can also be used [55].

A bifunctional linker may be used to provide a first group for coupling to an amine group in the glucan (e.g. introduced to the glucan by amination) and a second group for coupling to the carrier (typically for coupling to an amine in the carrier). Alternatively, the first group is capable of direct coupling to the glucan, i.e. without prior introduction of a group, e.g. an amine group, to the glucan.

In some embodiments, the first group in the bifunctional linker is thus able to react with an amine group (—$NH_2$) on the glucan. This reaction will typically involve an electrophilic substitution of the amine's hydrogen. In other embodiments, the first group in the bifunctional linker is able to react directly with the glucan. In both sets of embodiments, the second group in the bifunctional linker is typically able to react with an amine group on the carrier. This reaction will again typically involve an electrophilic substitution of the amine.

Where the reactions with both the glucan and the carrier involve amines then it is preferred to use a bifunctional linker. For example, a homobifunctional linker of the formula X-L-X may be used, where: the two X groups are the same as each other and can react with the amines; and where L is a linking moiety in the linker. Similarly, a heterobifunctional linker of the formula X-L-X may be used, where: the two X groups are different and can react with the amines; and where L is a linking moiety in the linker.

A preferred X group is N-oxysuccinimide. L preferably has formula L'-$L^2$-L', where L' is carbonyl. Preferred $L^2$ groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$) e.g. —$(CH_2)_4$— or —$(CH_2)_3$—.

Similarly, where the reaction with the glucan involves direct coupling and the reaction with the carrier involves an amine then it is also preferred to use a bifunctional linker. For example, a homobifunctional linker of the formula X-L-X may be used, where: the two X groups are the same as each other and can react with the glucan/amine; and where L is a linking moiety in the linker. Similarly, a heterobifunctional linker of the formula X-L-X may be used, where: the two X groups are different and one can react with the glucan while the other can react with the amine; and where L is a linking moiety in the linker. A preferred X group is N-oxysuccinimide. L preferably has formula L'-$L^2$-L', where L' is carbonyl. Preferred $L^2$ groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$) e.g. —$(CH_2)_4$— or —$(CH_2)_3$—.

Other X groups for use in the bifunctional linkers described in the two preceding paragraphs are those which form esters when combined with HO-L-OH, such as norborane, p-nitrobenzoic acid, and sulfo-N-hydroxysuccinimide.

Further bifunctional linkers for use with the invention include acryloyl halides (e.g. chloride) and haloacylhalides.

The linker will generally be added in molar excess to glucan during coupling to the glucan.

Preferred carrier proteins are bacterial toxins, such as diphtheria or tetanus toxins, or toxoids or mutants thereof. These are commonly used in conjugate vaccines. The $CRM_{197}$ diphtheria toxin mutant is particularly preferred [56].

Other suitable carrier proteins include the N. meningitidis outer membrane protein complex [57], synthetic peptides [58,59], heat shock proteins [60,61], pertussis proteins [62, 63], cytokines [64], lymphokines [64], hormones [64], growth factors [64], artificial proteins comprising multiple human $CD4^+$ T cell epitopes from various pathogen-derived antigens [65] such as N19 [66], protein D from H. influenzae [67-69], pneumolysin [70] or its non-toxic derivatives [71], pneumococcal surface protein PspA [72], iron-uptake proteins [73], toxin A or B from C. difficile [74], recombinant Pseudomonas aeruginosa exoprotein A (rEPA) [75], etc. It is possible to use mixtures of carrier proteins. A single carrier protein may carry multiple different glucans [76].

Conjugates may have excess carrier (w/w) or excess glucan (w/w) e.g. in the ratio range of 1:5 to 5:1. Conjugates with excess carrier protein are typical e.g. in the range 0.2:1 to 0.9:1, or equal weights. The conjugate may include small amounts of free (i.e. unconjugated) carrier. When a given carrier protein is present in both free and conjugated form in a composition of the invention, the unconjugated form is preferably no more than 5% of the total amount of the carrier protein in the composition as a whole, and more preferably present at less than 2% (by weight).

When the conjugate forms the glucan component in an immunogenic composition of the invention, the composition may also comprise free carrier protein as immunogen [77].

After conjugation, free and conjugated glucans can be separated. There are many suitable methods e.g. hydrophobic chromatography, tangential ultrafiltration, diafiltration, etc. [see also refs. 78, 79 etc.]. Tangential flow ultrafiltration is preferred.

The glucan moiety in the conjugate is preferably an low molecular weight glucan or an oligosaccharide, as defined above. Oligosaccharides will typically be sized prior to conjugation.

The protein-glucan conjugate is preferably soluble in water and/or in a physiological buffer.

The inventors have found that immunogenicity may be improved if there is a spacer between the glucan and the carrier protein. In this context, a "spacer" is a moiety that is longer than a single covalent bond. This spacer may be a linker, as described above. Alternatively, it may be a moiety covalently bonded between the glucan and a linker. Typically, the moiety will be covalently bonded to the glucan prior to coupling to the linker or carrier. For example, the spacer may be moiety Y, wherein Y comprises a straight chain alkyl with 1 to 10 carbon atoms (e.g. $C_1$, $C_2$, $C_3$, $C_4$, $C_5$, $C_6$, $C_7$, $C_8$, $C_9$, $C_{10}$), typically 1 to 6 carbon atoms (e.g. $C_1$, $C_2$, $C_3$, $C_4$, $C_5$, $C_6$). The inventors have found that a straight chain alkyl with 6 carbon atoms (i.e. —$(CH_2)_6$) is particularly suitable, and may provide greater immunogenicity than shorter chains (e.g. —$(CH_2)_2$). Typically, Y is attached to the anomeric carbon of the glucan, usually via an —O— linkage. However, Y may be linked to other parts of the glucan and/or via other linkages. The other end of Y is bonded to the linker by any suitable linkage. Typically, Y terminates with an amine group to facilitate linkage to a bifunctional linker as described above. In these embodiments, Y is therefore bonded to the linker by an —NH— linkage. Accordingly, a conjugate with the following structure is specifically envisaged for use in the present invention:

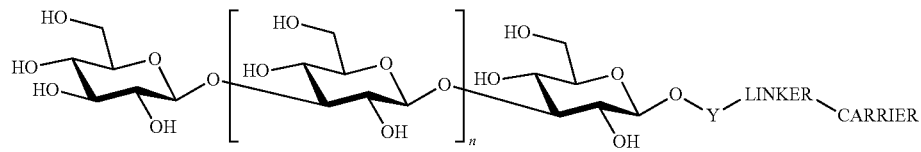

wherein n+2 is in the range of 2-60, e.g. between 10-50 or between 20-40. Preferably, n+2 is in the range of 25-30 or 11-19, e.g. 13-17. The inventors have found that n+2=15 is suitable. Y is as described above. "LINKER" is an optional linker as described above, while "CARRIER" is a carrier molecule as described above.

Pharmaceutical Compositions

The invention provides a pharmaceutical composition comprising (a) a glucan or conjugate of the invention, and (b) a pharmaceutically acceptable carrier. A thorough discussion of such carriers is available in reference 80.

Microbial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops, as a spray, or as a powder [e.g. 81]. The composition may be included in a mouthwash. The composition may be lyophilised.

The pharmaceutical composition is preferably sterile. It is preferably pyrogen-free. It is preferably buffered e.g. at between pH 6 and pH 8, generally around pH 7.

The invention also provides a delivery device containing a pharmaceutical composition of the invention. The device may be, for example, a syringe or an inhaler.

Pharmaceutical compositions of the invention are preferably immunogenic compositions, in that they comprise an immunologically effective amount of a glucan immunogen. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses). The composition may be administered in conjunction with other immunoregulatory agents.

Once formulated, the compositions of the invention can be administered directly to the subject. The subjects to be treated can be animals; in particular, human subjects can be treated.

Immunogenic compositions of the invention may be used therapeutically (i.e. to treat an existing infection) or prophylactically (i.e. to prevent future infection). Therapeutic immunisation is particularly useful for treating *Candida* infection in immunocompromised subjects.

Even though β-glucans have themselves been reported to be adjuvants, an immunogenic composition may include a further adjuvant, which can function to enhance the immune responses (humoral and/or cellular) elicited in a patient who receives the composition. Adjuvants that can be used with the invention include, but are not limited to:

A mineral-containing composition, including calcium salts and aluminum salts (or mixtures thereof). Calcium salts include calcium phosphate (e.g. the "CAP" particles disclosed in ref. 82). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [83]. The adjuvants known as aluminum hydroxide and aluminum phosphate may be used. These names are conventional, but are used for convenience only, as neither is a precise description of the actual chemical compound which is present (e.g. see chapter 9 of reference 166). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc. The concentration of $Al^{+++}$ in a composition for administration to a patient is preferably less than 10 mg/ml e.g. ≥5 mg/ml, ≥4 mg/ml, ≥3 mg/ml, ≥2 mg/ml, ≥1 mg/ml, etc. A preferred range is between 0.3 and 1 mg/ml. A maximum of 0.85 mg/dose is preferred.

Saponins [chapter 22 of ref. 166], which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 84. Saponin formulations may also comprise a sterol, such as cholesterol [85]. Combinations of saponins and cholesterols can be used to form unique particles called immunostimulating complexs (ISCOMs) [chapter 23 of ref. 166]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 85-87. Optionally, the ISCOMS may be devoid of additional detergent [88]. A review of the development of saponin based adjuvants can be found in refs. 89 & 90.

Bacterial ADP-ribosylating toxins (e.g. the *E. coli* heat labile enterotoxin "LT", cholera toxin "CT", or pertussis toxin "PT") and detoxified derivatives thereof, such as the mutant toxins known as LT-K63 and LT-R72 [91]. The use of detoxified ADP-ribosylating toxins as mucosal adjuvants is described in ref. 92 and as parenteral adjuvants in ref. 93.

Bioadhesives and mucoadhesives, such as esterified hyaluronic acid microspheres [94] or chitosan and its derivatives [95].

Microparticles (i.e. a particle of ~100 nm to ~150 μm in diameter, more preferably ~200 nm to ~30 μm in diameter, or ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) being preferred, optionally treated to have a negatively-charged surface (e.g. with SDS) or a positively-charged surface (e.g. with a cationic detergent, such as CTAB).

Liposomes (Chapters 13 &. 14 of ref. 166). Examples of liposome formulations suitable for use as adjuvants are described in refs. 96-98.

Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™"), N-acetylmuramyl-L-alanyl-D-isoglutaminyl-L-alanine-2-(1'-2' dipalmitoyl-sn-glycero-3-hydroxyphosphoryloxy)-ethylamine ("MTP-PE").

A polyoxidonium polymer [99,100] or other N-oxidized polyethylene-piperazine derivative.

Methyl inosine 5'-monophosphate ("MIMP") [101].

A polyhydroxlated pyrrolizidine compound [102], such as one having formula:

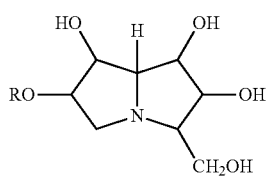

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A CD1d ligand, such as an α-glycosylceramide [103-110] (e.g. α-galactosylceramide), phytosphingosine-containing α-glycosylceramides, OCH, KRN7000 [(2S,3S,4R)-1-O-(α-D-galactopyranosyl)-2-(N-hexacosanoy-lamino)-1,3,4-octadecanetriol], CRONY-101, 3"-O-sulfo-galactosylceramide, etc.

A gamma inulin [111] or derivative thereof, such as algammulin.

An oil-in-water emulsion. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with a size less than 220 nm are preferred as they can be subjected to filter sterilization.

An immunostimulatory oligonucleotide, such as one containing a CpG motif (a dinucleotide sequence containing an unmethylated cytosine residue linked by a phosphate bond to a guanosine residue), or a CpI motif (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded. References 112, 113 and 114 disclose possible analog substitutions e.g. replacement of guanosine with 2'-deoxy-7-deazaguanosine. The adjuvant effect of CpG oligonucleotides is further discussed in refs. 115-120. A CpG sequence may be directed to TLR9, such as the motif GTCGTT or TTCGTT [121]. The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. 122-124. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 121 & 125-127. A useful CpG adjuvant is CpG7909, also known as ProMune™ (Coley Pharmaceutical Group, Inc.). Another is CpG1826. As an alternative, or in addition, to using CpG sequences, TpG sequences can be used [128], and these oligonucleotides may be free from unmethylated CpG motifs. The immunostimulatory oligonucleotide may be pyrimidine-rich. For example, it may comprise more than one consecutive thymidine nucleotide (e.g. TTTT, as disclosed in ref. 128), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in ref. 128), and/or it may have a nucleotide composition with >25% cytosine (e.g. >35%, >40%, >50%, >60%, >80%, etc.). These oligonucleotides may be free from unmethylated CpG motifs. Immunostimulatory oligonucleotides will typically comprise at least 20 nucleotides. They may comprise fewer than 100 nucleotides.

A particularly useful adjuvant based around immunostimulatory oligonucleotides is known as IC31™ [129]. Thus an adjuvant used with the invention may comprise a mixture of (i) an oligonucleotide (e.g. between 15-40 nucleotides) including at least one (and preferably multiple) CpI motifs, and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 1). The polycationic polymer may be a peptide comprising 11-mer amino acid sequence KLKLLLLLKLK (SEQ ID NO: 2).

- 3-O-deacylated monophosphoryl lipid A ('3dMPL', also known as 'MPL™') [130-133]. In aqueous conditions, 3dMPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3dMPL) are preferred for use according to the invention because of their superior activity [134]. Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm.
- An imidazoquinoline compound, such as Imiquimod ("R-837") [135,136], Resiquimod ("R-848") [137], and their analogs; and salts thereof (e.g. the hydrochloride salts). Further details about immunostimulatory imidazoquinolines can be found in references 138 to 142.
- A thiosemicarbazone compound, such as those disclosed in reference 143. Methods of formulating, manufacturing, and screening for active compounds are also described in reference 143. The thiosemicarbazones are particularly effective in the stimulation of human peripheral blood mononuclear cells for the production of cytokines, such as TNF-α.
- A tryptanthrin compound, such as those disclosed in reference 144. Methods of formulating, manufacturing, and screening for active compounds are also described in reference 144. The thiosemicarbazones are particularly effective in the stimulation of human peripheral blood mononuclear cells for the production of cytokines, such as TNF-α.
- A nucleoside analog, such as: (a) Isatorabine (ANA-245; 7-thia-8-oxoguanosine):

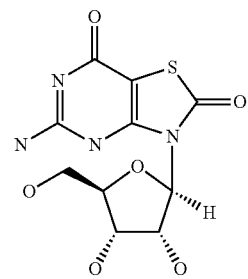 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 1 to 3Loxoribine (7-allyl-8-oxoguanosine) [148].

- Compounds disclosed in reference 149, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [150-151], Hydrapthalamide compounds, Benzophenone compounds, Isoxazole compounds, Sterol compounds, Quinazilinone compounds, Pyrrole compounds [152], Anthraquinone compounds, Quinoxaline compounds, Triazine compounds, Pyrazalopyrimidine compounds, and Benzazole compounds [153].

- An aminoalkyl glucosaminide phosphate derivative, such as RC-529 [154, 155].

- A phosphazene, such as poly[di(carboxylatophenoxy) phosphazene] ("PCPP") as described, for example, in references 156 and 157.

- A substituted urea or compound of formula I, II or III, or a salt thereof:

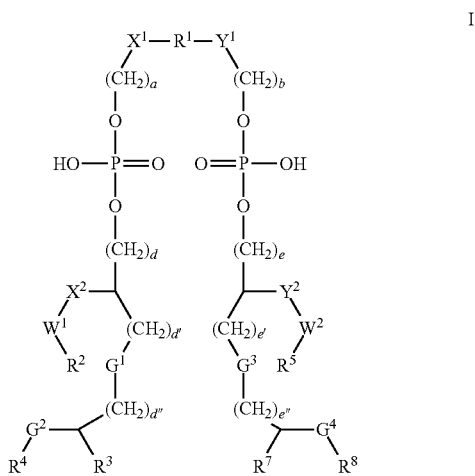

I

-continued
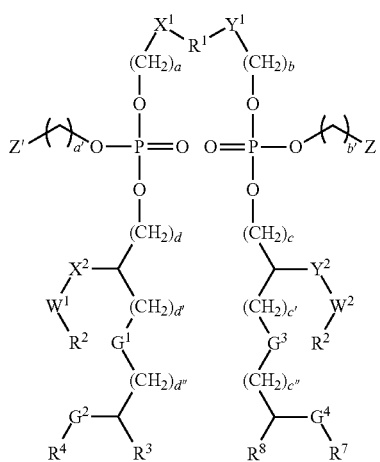
II
-continued
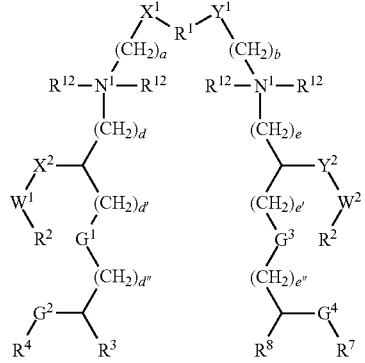
III
as defined in reference 158, such as 'ER 803058', 'ER 803732', 'ER 804053', ER 804058', 'ER 804059', 'ER 804442', 'ER 804680', 'ER 804764', ER 803022 or 'ER 804057' e.g.:
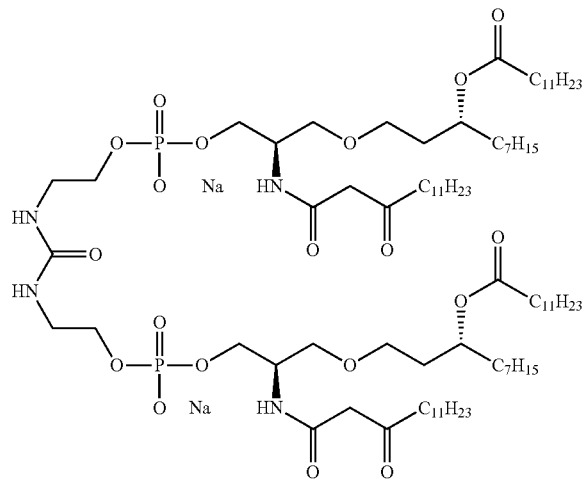
ER804057
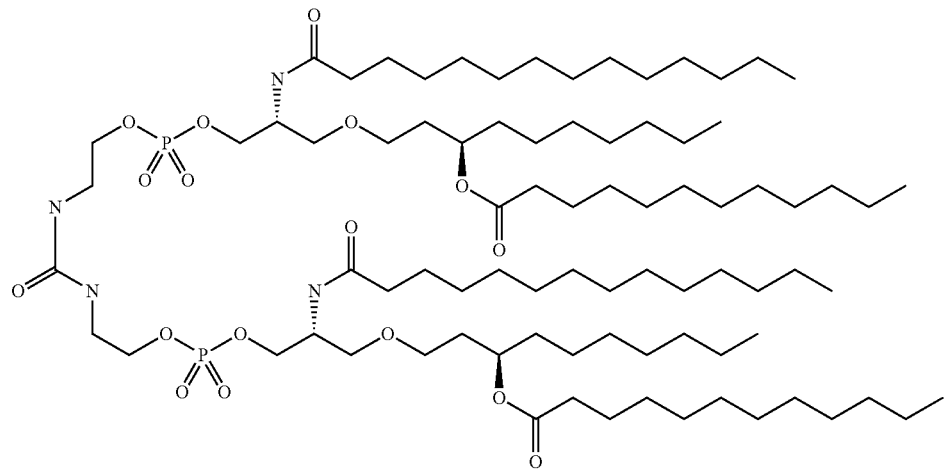
ER-803022

Derivatives of lipid A from *Escherichia coli* such as OM-174 (described in refs. 159 & 160).

Compounds containing lipids linked to a phosphate-containing acyclic backbone, such as the TLR4 antagonist E5564 [161, 162]:

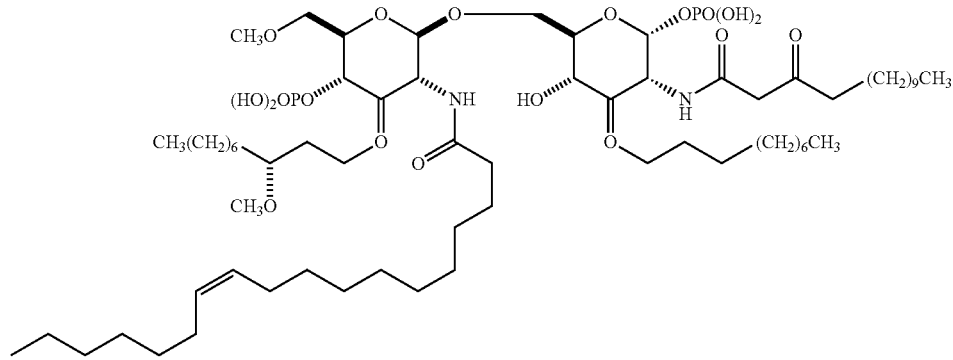

These and other adjuvant-active substances are discussed in more detail in references 166 & 167.

Antigens and adjuvants in a composition will typically be in admixture.

Compositions may include two or more of said adjuvants. For example, they may advantageously include both an oil-in-water emulsion and 3dMPL, etc.

Specific oil-in-water emulsion adjuvants useful with the invention include, but are not limited to:

A submicron emulsion of squalene, TWEEN 80, and SPAN 85. The composition of the emulsion by volume can be about 5% squalene, about 0.5% polysorbate 80 and about 0.5% SPAN 85. In weight terms, these ratios become 4.3% squalene, 0.5% polysorbate 80 and 0.48% SPAN 85. This adjuvant is known as 'MF59' [163-165], as described in more detail in Chapter 10 of ref. 166 and chapter 12 of ref. 167. The MF59 emulsion advantageously includes citrate ions e.g. 10 mM sodium citrate buffer.

An emulsion of squalene, a tocopherol, and TWEEN 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% TWEEN 80, and the weight ratio of squalene:tocopherol is preferably ≤1 as this provides a more stable emulsion. Squalene and TWEEN 80 may be present at a volume ratio of about 5:2. One such emulsion can be made by dissolving TWEEN 80 in PBS to give a 2% solution, then mixing 90 ml of this solution with a mixture of 5 g of DL-.alpha.-tocopherol and 5 ml squalene, then microfluidising the mixture. The resulting emulsion may have submicron oil droplets e.g. with an average diameter of between 100 and 250 nm, preferably about 180 nm.

An emulsion of squalene, a tocopherol, and a TRITON detergent (e.g. TRITON X-100). The emulsion may also include a 3d-MPL (see below). The emulsion may contain a phosphate buffer.

An emulsion comprising a polysorbate (e.g. polysorbate 80), a TRITON detergent (e.g. TRITON X-100) and a tocopherol (e.g. an α-tocopherol succinate). The emulsion may include these three components at a mass ratio of about 75:11:10 (e.g. 750 μg/ml polysorbate 80, 110 μg/ml TRITON X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("PLURONIC™ L121"). The emulsion can be formulated in phosphate buffered saline, pH 7.4. This emulsion is a useful delivery vehicle for muramyl dipeptides, and has been used with threonyl-MDP in the "SAF-1" adjuvant [168] (0.05-1% Thr-MDP, 5% squalane, 2.5% PLURONIC L121 and 0.2% polysorbate 80). It can also be used without the Thr-MDP, as in the "AF" adjuvant [169] (5% squalane, 1.25% PLURONIC L121 and 0.2% polysorbate 80). Microfluidisation is preferred.

An emulsion having from 0.5-50% of an oil, 0.1-10% of a phospholipid, and 0.05-5% of a non-ionic surfactant. As described in reference 170, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, TWEEN 80 or SPAN 80). Additives may be included, such as QuilA saponin, cholesterol, a saponin-lipophile conjugate (such as GPI-0100, described in reference 171, produced by addition of aliphatic amine to desacylsaponin via the carboxyl group of glucuronic acid), dimethyldioctadecylammonium bromide and/or N,N-dioctadecyl-N,N-bis(2-hydroxyethyl)propanediamine.

An emulsion in which a saponin (e.g. QuilA or QS21) and a sterol (e.g. a cholesterol) are associated as helical micelles [172].

Medical Treatments and Uses

The invention also provides a glucan or conjugate of the invention, for use in medicine e.g. for use in raising an antibody response in a mammal.

The invention also provides a method for raising an immune response in a mammal, comprising administering a glucan, conjugate or pharmaceutical composition of the invention to the mammal.

The invention also provides the use of a glucan or conjugate of the invention in the manufacture of a medicament for preventing or treating a microbial infection in a mammal.

The immune response raised by these methods and uses will generally include an antibody response, preferably a protective antibody response. Methods for assessing antibody responses after saccharide immunisation are well known in the art. The antibody response is preferably an IgA or IgG response. The immune response may be prophylactic and/or therapeutic. The mammal is preferably a human.

Because glucans (and β-glucans in particular) are an essential and principal polysaccharide constituent of almost all pathogenic fungi, particularly those involved in infections in immunocompromised subjects, and also in bacterial pathogens and protozoa, anti-glucan immunity may have efficacy against a broad range of pathogens and diseases. For example, anti-glucan serum raised after immunisation with *S. cerevisiae* is cross-reactive with *C. albicans*. Broad spectrum immunity is particularly useful because, for these human infectious fungal agents, chemotherapy is scanty, antifungal drug resistance is emerging and the need for preventative and therapeutic vaccines is increasingly recognized.

The uses and methods of the invention are particularly useful for treating/protecting against infections of: *Candida* species, such as *C. albicans*; *Cryptococcus* species, such as *C. neoformans*; *Enterococcus* species, such as *E. faecalis*; *Streptococcus* species, such as *S. pneumoniae*, *S. mutans*, *S. agalactiae* and *S. pyogenes*; *Leishmania* species, such as *L. major*; *Acanthamoeba* species, such as *A. castellani*; *Aspergillus* species, such as *A. fumigatus* and *A. flavus*; *Pneumocystis* species, such as *P. carinii*; *Mycobacterium* species, such as *M. tuberculosis*; *Pseudomonas* species, such as *P. aeruginosa*; *Staphylococcus* species, such as *S. aureus*; *Salmonella* species, such as *S. typhimurium*; *Coccidioides* species such as *C. immitis*; *Trichophyton* species such as *T. verrucosum*; *Blastomyces* species such as *B. dermatidis*; *Histoplasma* species such as *H. capsulatum*; *Paracoccidioides* species such as *P. brasiliensis*; *Pythium* species such as *P. insidiosum*; and *Escherichia* species, such as *E. coli*.

The uses and methods are particularly useful for preventing/treating diseases including, but not limited to: candidiasis (including hepatosplenic candidiasis, invasive candidiasis, chronic mucocutaneous candidiasis and disseminated candidiasis); candidemia; aspergillosis, cryptococcosis, dermatomycoses, sporothrychosis and other subcutaneous mycoses, blastomycosis, histoplasmosis, coccidiomycosis, paracoccidiomycosis, pneumocystosis, thrush, tuberculosis, mycobacteriosis, respiratory infections, scarlet fever, pneumonia, impetigo, rheumatic fever, sepsis, septicaemia, cutaneous and visceral leishmaniasis, corneal acanthamoebiasis, cystic fibrosis, typhoid fever, gastroenteritis and hemolytic-uremic syndrome. Anti-*C. albicans* activity is particularly useful for treating infections in AIDS patients.

Efficacy of therapeutic treatment can be tested by monitoring microbial infection after administration of the composition of the invention. Efficacy of prophylactic treatment can be tested by monitoring immune responses against β-glucan (e.g. anti-β-glucan antibodies) after administration of the composition.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intradermal, ocular, nasal, aural, or pulmonary administration. Injection or intranasal administration is preferred.

The invention may be used to elicit systemic and/or mucosal immunity.

Vaccines prepared according to the invention may be used to treat both children and adults. Thus a subject may be less than 1 year old, 1-5 years old, 5-15 years old, 15-55 years old, or at least 55 years old. Preferred subjects for receiving the vaccines are the elderly (e.g. ≥50 years old, ≥60 years old, and preferably ≥65 years), or the young (e.g. ≤5 years old). The vaccines are not suitable solely for these groups, however, and may be used more generally in a population.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Conjugates of the invention may be combined with non-glucan antigens into a single composition for simultaneous immunisation against multiple pathogens. As an alternative to making a combined vaccine, conjugates may be administered to patients at substantially the same time as (e.g. during the same medical consultation or visit to a healthcare professional or vaccination centre) other vaccines. Antigens for use in these combination vaccines or for concomitant administration include, for instance, immunogens from *Streptococcus agalactiae*, *Staphylococcus aureus* and/or *Pseudomonas aeuruginosa*, hepatitis A virus, hepatitis B virus, *Neisseria meningitidis* (such as saccharides or conjugated saccharides, for serogroups A, C, W135 and/or Y), *Streptococcus pneumoniae* (such as saccharides or conjugated saccharides), etc.

Compositions of the invention may be used in conjunction with anti-fungals, particularly where a patient is already infected. The anti-fungal offers an immediate therapeutic effect whereas the immunogenic composition offers a longer-lasting effect. Suitable anti-fungals include, but are not limited to, azoles (e.g. fluconazole, itraconazole), polyenes (e.g. amphotericin B), flucytosine, and squalene epoxidase inhibitors (e.g. terbinafine) [see also ref. 173]. The anti-fungal and the immunogenic composition may be administered separately or in combination. When administered separately, they will typically be administered within 7 days of each other. After the first administration of an immunogenic composition, the anti-fungal may be administered more than once.

Definitions

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x+10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

MODES FOR CARRYING OUT THE INVENTION

Curdlan Conjugation (1)

Curdlan with a starting MW of >100 kDa was treated by acid hydrolysis using HCl (0.5M) in DMSO for 10 minutes at 85° C. The hydrolysate had a DP around 25 units.

Hydrolysed material was neutralised with sodium phosphate buffer (400 mM, pH 6.8) and diluted with water to give a 10:1 dilution of the starting material. The final concentration was 1 mg/ml. After dilution, some precipitation was detectable. The precipitates are probably high MW saccharide.

Ammonium acetate was added and then sodium cyanoborohydride. After adjusting the pH to 7.0 the mixture was incubated at 37° C. for 3-5 days. This treatment introduced a primary amino group at the reducing terminus of the curdlan fragments. The amino-saccharides were then purified by ultrafiltration with a 3 kDa cut-off membrane. Amino groups were estimated by the Habeeb method.

Dried amino-oligosaccharide was solubilised in distilled water at a 40 mM amino group concentration, then 9 volumes of DMSO were added followed by triethyl-amine at a final concentration of 200 mM. To the resulting solution, adipic acid N-hydroxysuccinimido diester was added for a final concentration of 480 mM. Ester groups generated in this way were estimated by analysis of released N-hydroxysuccinimido groups.

Dried activated oligosaccharide was added to $CRM_{197}$ in 10 mM phosphate buffer pH 7.0. The reaction was maintained under stirring at room temperature overnight. The final material had a ratio of about 50:1 in term of mol of N-hydroxysuccinimido ester per mol of protein.

The conjugate was then purified by ultrafiltration with a 30 kDa cut-off membrane. The conjugate was characterized by SDS-Page, SEC-HPLC and NMR. Also, the saccharide (total and un-conjugated saccharide) and protein content were estimated.

Conjugates were prepared in the same way, but with tetanus toxoid as the carrier instead of CRM197.

For five prepared lots of conjugates, the saccharide:protein ratios were as follows (excess carrier):

| | Lot | | | | |
|---|---|---|---|---|---|
| | 1 | 2 | 3 | 4 | 5 |
| Carrier | CRM197 | CRM197 | CRM197 | CRM197 | Tt |
| Ratio | 0.46:1 | 0.25:1 | 0.45:1 | 0.35:1 | 0.29:1 |

FIG. 1 shows SDS-PAGE of example conjugates, and FIG. 2 shows their SEC-HPLC profiles.

Conjugation (2)

Synthetic curdlan (15-mer) and laminarin (17-mer) conjugates were prepared according to the method described in FIG. 3. Briefly, the indicated synthetic oligosaccharides were solubilised in distilled water at a concentration of 40 mM amino groups. Nine volumes of DMSO were then added, followed by triethylamine to a final concentration of 200 mM. For the 15-mer-C6 β(1-3)-CRM conjugate, glutarate N-hydroxysuccinimido diester was added to a final concentration of 240 mM. For the 15-mer-C6 β(1-3)-CRM and 17-mer-C6 β(1-3)-CRM conjugates, adipic acid N-hydroxysuccinimido diester was added to a final concentration of 480 mM. The activated oligosaccharides were then purified by precipitation with 80% v/v dioxane. The number of ester groups generated in each reaction was estimated by measuring the amount of released N hydroxy-succinimido groups. Dried, activated oligosaccharides were then added to a 30 mg/mL CRM197 solution in 10 mM phosphate buffer at pH 7.2. The reaction was maintained under stirring at room temperature overnight. The final materials had a ratio of about 50:1 in terms of moles of N-hydroxysuccinimido ester per mole of protein.

The conjugates were then characterized by SDS-Page and SEC-HPLC. The saccharide and protein contents were estimated as follows:

| Sample | Conc sacc (mg/mL) | Conc prot (mg/mL) | Sacc/prot (% w/w) | Sacc/prot (mol/mol) |
|---|---|---|---|---|
| 15-mer-C6 β(1-3)-CRM | 923.1 | 1695.5 | 54.4 | 11.7 |
| 15-mer-C2 β(1-3)-CRM | 651.7 | 2071.0 | 31.5 | 6.8 |
| 17-mer-C2 β(1-3)-CRM | 2113.7 | 4096.0 | 51.7 | 9.8 |

Figure 4:
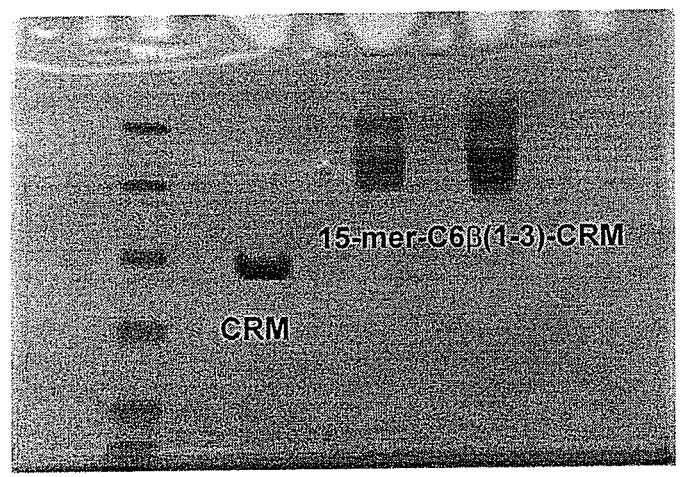
FIGS. 4A and 4B show an SDS-PAGE analysis of conjugates of synthetic glucans.
Figure 4:
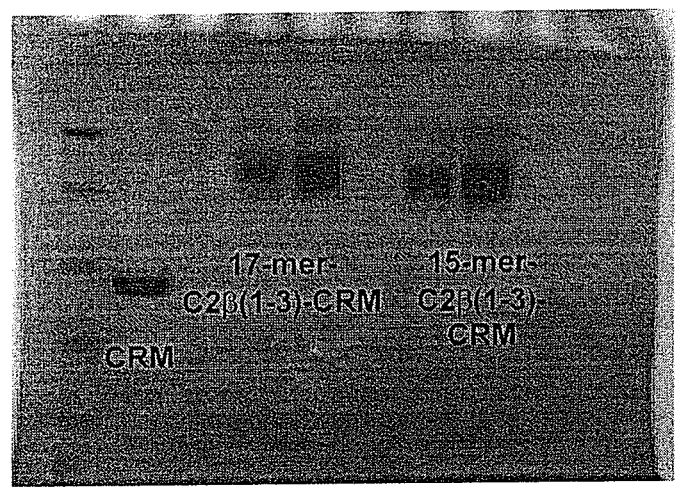

FIGS. 4A and 4B illustrate an SDS-PAGE analysis of these conjugates on a 7% tris-acetate gel (20 µg loaded per well).

Immunogenicity Study (1)

Curdlan conjugates prepared as described in Curdlan conjugation (1) were administered to mice in immunogenicity studies, and were compared to laminarin-CRM197 conjugates prepared as described in the prior art, e.g. as in references 174 and 175. More than one lot of curdlan conjugates was tested CD2F1 mice, 4-6 weeks old, were tested in 18 groups of 10. The conjugates were used at a saccharide dose of 5 µg in a dosage volume of 150 µl, administered intraperitoneally at days 1, 7 and 21. Blood samples were taken on days 0, 21 and 35 for assessing anti-GGZym antibody levels by ELISA [3,4].

Conjugates were administered either without adjuvant or with the following adjuvants: (a) an aluminium hydroxide adjuvant; (b) the MF59 oil-in-water emulsion adjuvant; (c) a combination of (a) with 10 µg of a CpG oligodeoxynucleotide; (d) a combination of (b) with a CpG oligodeoxynucleotide.

Anti-glucan antibodies (GMT) and the number of responding mice (%) at day 35 are reported in Table 1.

TABLE 1

| Group | Glucan | Adjuvant | GMT | % responders |
|---|---|---|---|---|
| 1 | Laminarin | — | 13 | 57 |
| 2 | | Alum | 55 | 80 |
| 3 | | Alum + CpG | 405 | 100 |
| 4 | | | | |
| 5 | | MF59 | 26 | 70 |
| 6 | | MF59 + CpG | 282 | 90 |
| 7 | | | | |
| 8 | | | | |
| 9 | Curdlan | — | 4 | 20 |
| 10 | | — | 6 | 25 |
| 11 | | Alum | 318 | 90 |
| 12 | | Alum + CpG | 458 | 90 |
| 13 | | | | |
| 14 | | MF59 | 322 | 90 |

TABLE 1-continued

| Group | Glucan | Adjuvant | GMT | % responders |
|---|---|---|---|---|
| 15 | | MF59 + CpG | 148 | 90 |
| 16 | | | | |
| 17 | | | | |
| 18 | | — | 3 | 10 |

The curdlan conjugates are generally more immunogenic than the laminarin conjugates.

Immunogenicity Study (2)

In further experiments, laminarin and curdlan conjugates prepared as described in Immunogenicity study (1) were also adjuvanted with α-galactosylceramide (100 ng) or LT-K63 (2 μg), either alone or in combination with other adjuvants. The CpG adjuvant was also tested at three different doses (0.5 μg, 5 μg and 10 μg). Details were as in the previous immunogenicity study, but with 8 mice per group. Results are in Table 2.

TABLE 2

| Group | Glucan | Adjuvant | GMT | % responders |
|---|---|---|---|---|
| 1 | Laminarin | — | 2 | 0 |
| 2 | | Alum | 15 | 57 |
| 3 | | LT-K63 | 10 | 43 |
| 4 | | MF59 | 8 | 25 |
| 5 | | α-GalCer | 28 | 57 |
| 6 | | Alum + α-GalCer | 384 | 100 |
| 7 | | MF59 + α-GalCer | 176 | 75 |
| 8 | | Alum + CpG$_{10\mu g}$ | 84 | 75 |
| 9 | | Alum + CpG$_{5\mu g}$ | 407 | 100 |
| 10 | | Alum + CpG$_{0.5\mu g}$ | 133 | 71 |
| 11 | Curdlan | — | 6 | 38 |
| 12 | | Alum | 70 | 75 |
| 13 | | LT-K63 | 262 | 86 |
| 14 | | MF59 | 20 | 63 |
| 15 | | α-GalCer | 783 | 100 |
| 16 | | Alum + α-GalCer | 443 | 100 |
| 17 | | MF59 + α-GalCer | 386 | 100 |

Again, the curdlan conjugates are generally more immunogenic than the laminarin conjugates.

Immunogenicity Study (3)

In further work, laminarin or curdlan conjugated to either CRM197 or tetanus toxoid were combined with various individual and combined adjuvants and administered to mice by subcutaneous or intrapertioneal administration. The conjugates were prepared as described in Immunogenicity study (1).

CD2F1 mice, 4-6 weeks old, were tested in 12 groups of 10. The conjugates were used at a saccharide dose of 5 μg in a dosage volume of 150 μl, administered days 1, 14 and 28 by subcutaneous or intrapertioneal administration. Blood samples were taken on days 0, 28 and 42 for assessing anti-GGZym antibody levels by ELISA.

Groups 1-3 received three identical doses of laminarin conjugated to CRM197 with the following adjuvants: (a) an aluminium hydroxide adjuvant (300 μg); (b) a combination of (a) and a CpG oligodeoxynucleotide, CpG1826 (10 μg); and (c) the MF59 oil-in-water emulsion adjuvant (75 μl), respectively. Groups 4-6 were treated in the same way as groups 1-3 respectively, except that the glucan was curdlan instead of laminarin. Groups 7-9 were treated in the same way as groups 1-3 respectively, except that the laminarin was conjugated to tetanus toxoid instead of CRM197. Similarly, groups 10-12 were treated in the same way as groups 4-6 respectively, except that the curdlan was conjugated to tetanus toxoid instead of CRM197.

Figure 5:
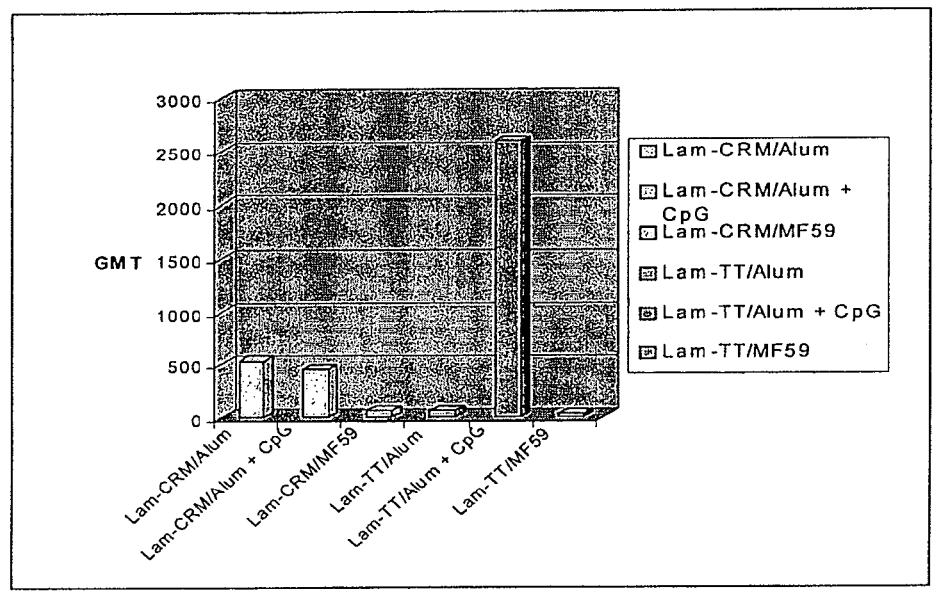
FIG. 5 shows IgG GMT against laminarin conjugated to either CRM197 or tetanus toxoid combined with various individual and combined adjuvants administered by intrapertioneal administration.
Figure 6:
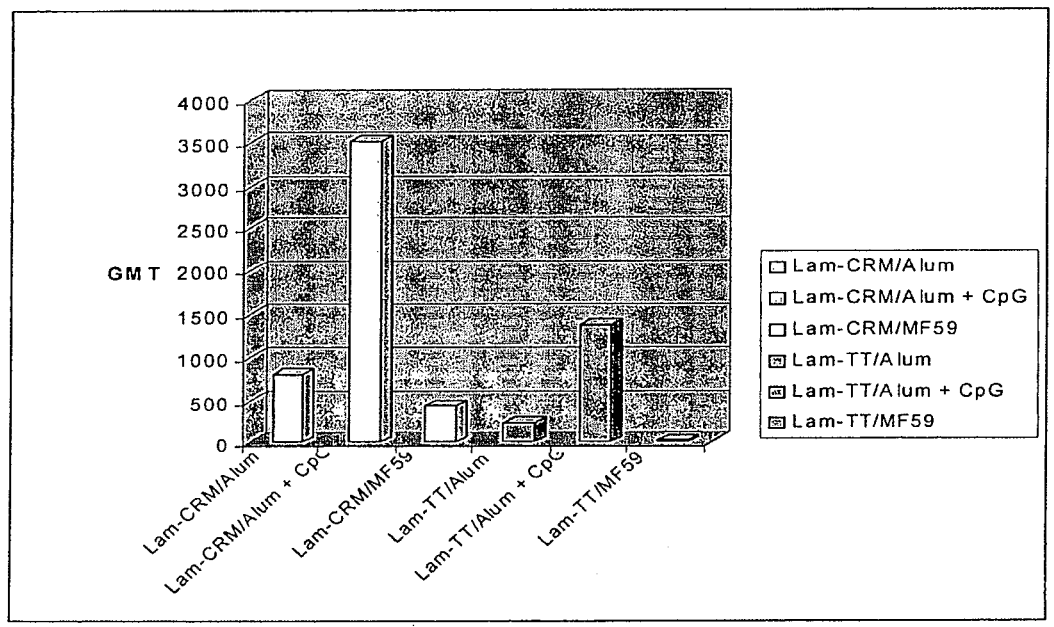
FIG. 6 shows IgG GMT against laminarin conjugated to either CRM197 or tetanus toxoid combined with various individual and combined adjuvants administered by subcutaneous administration.

Anti-glucan antibodies (GMT) at day 42 after intrapertioneal administration of laminarin conjugates to the mice are shown in FIG. 5. The corresponding results after subcutaneous administration are shown in FIG. 6. The results show that a better response was generally seen when the conjugates were administered by subcutaneous administration. Moreover, better results were generally obtained using CRM197 as the carrier protein, particularly when the conjugates were administered by subcutaneous administration.

Figure 7:
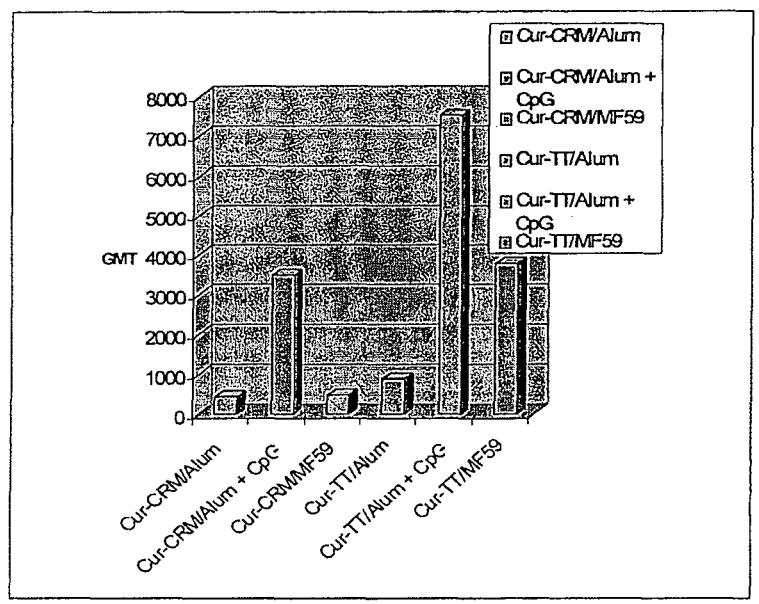
FIG. 7 shows IgG GMT against curdlan conjugated to either CRM197 or tetanus toxoid combined with various individual and combined adjuvants administered by intrapertioneal administration.
Figure 8:
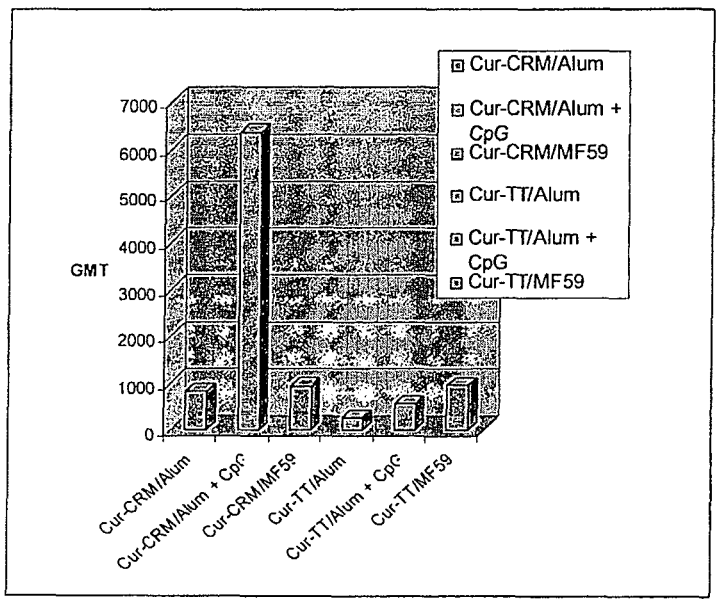
FIG. 8 shows IgG GMT against curdlan conjugated to either CRM197 or tetanus toxoid combined with various individual and combined adjuvants administered by subcutaneous administration.

Similarly, anti-glucan antibodies (GMT) at day 42 after intrapertioneal administration of curdlan conjugates are shown in FIG. 7. The corresponding results after subcutaneous administration are shown in FIG. 8. When CRM197 was used as the carrier protein, a better response was seen when the conjugates were administered by subcutaneous administration.

Immunogenicity Study (4)

In another study, laminarin or curdlan conjugated to CRM197 were administered to mice using different doses of saccharide. The conjugates were prepared as described in Immunogenicity study (1).

CD2F1 mice, 4-6 weeks old, were tested in 12 groups of 8. The conjugates were used at a saccharide doses of 10 μg, 5 μg, 1 μg or 0.1 μg in a dosage volume of 150 μl, administered days 1, 14 and 28. Blood samples were taken on days 0, 28 and 42 for assessing anti-GGZym antibody levels by ELISA. Anti-laminarin antibody levels were also measured by substituting laminarin for GG-Zym in the ELISA, as described in reference 175.

Group 1 received three identical doses of laminarin conjugated to CRM197 with no adjuvant and a saccharide dose of 5 μg. Group 2 received three identical doses of laminarin conjugated to CRM197 with an aluminium hydroxide adjuvant (300 μg) and a saccharide dose of 5 μg. A phosphate buffer had been used during the purification of the conjugate administered to this group. Groups 3-6 received three identical doses of laminarin conjugated to CRM197 with an aluminium hydroxide adjuvant (300 μg) and a saccharide dose of 10 μg, 5 μg, 1 μg or 0.1 μg, respectively. A histidine buffer had been used during the purification of the conjugates administered to these groups, as described in reference 176.

Groups 7-12 were treated in the same way as groups 1-6, except that the glucan was curdlan instead of laminarin.

Figure 9:
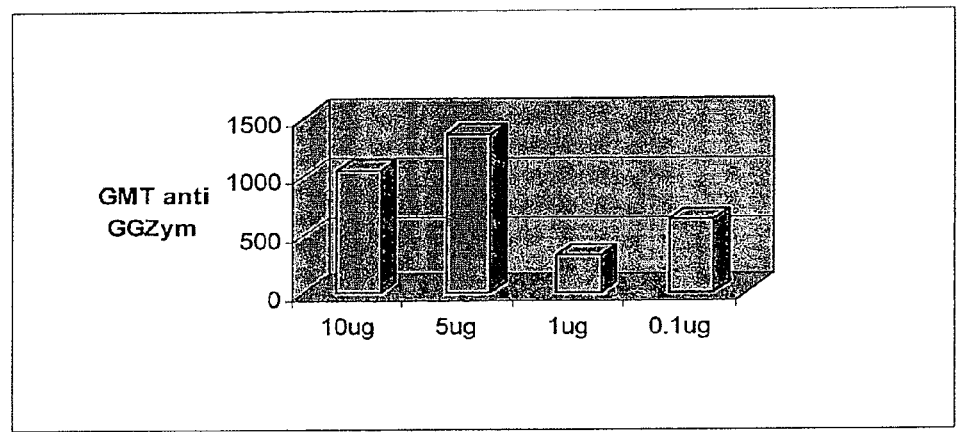
FIG. 9 shows IgG GMT against laminarin conjugates at various saccharide doses.

Anti-glucan antibodies (GMT) at day 42 after administration of laminarin conjugates at various saccharide doses are shown in FIG. 9. The results show that a response was seen at all doses, with the best response being obtained with a saccharide dose of 5 μg.

Figure 10:
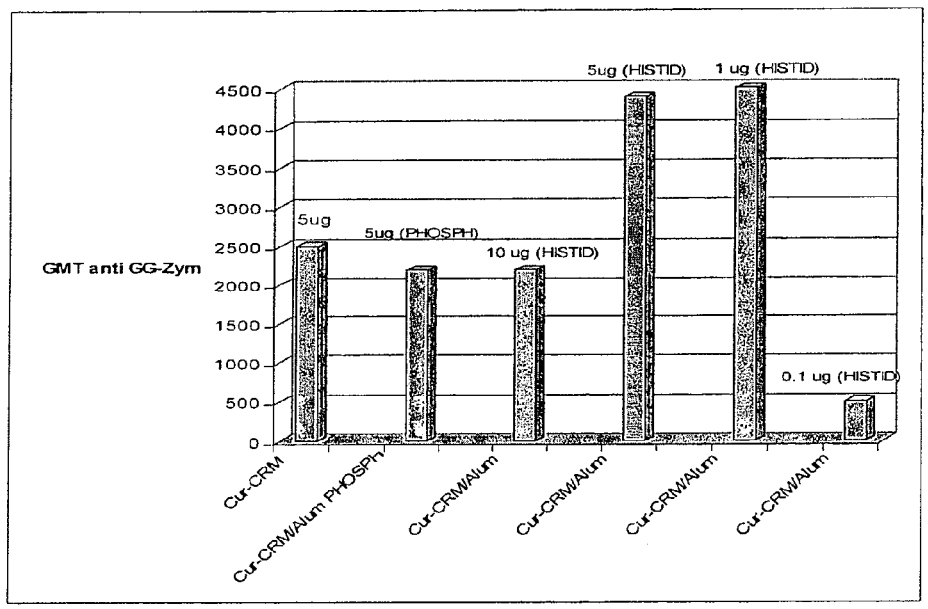
FIG. 10 shows IgG GMT against curdlan conjugates alone or combined with individual adjuvants at various saccharide doses.

Anti-glucan antibodies (GMT) at day 42 after administration of the curdlan conjugates are shown in FIG. 10. Once again, the results show that a response was seen at all doses of saccharide. The best responses were obtained with saccharide doses of 10 μg and 5 μg.

Figure 11:
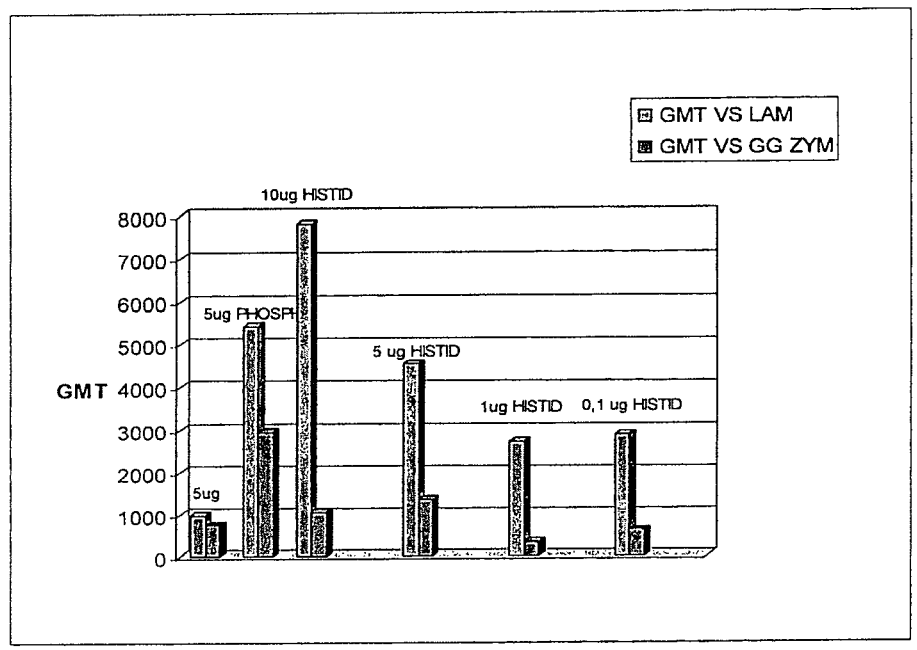
FIG. 11 shows IgG GMT (anti-GGZym and anti-laminarin) against laminarin conjugates alone or combined with individual adjuvants at various saccharide doses.

Anti-glucan antibodies (GMT) at day 42 after administration of the laminarin conjugates are shown in FIG. 11. The results obtained using the anti-GGZym antibody ELISA are compared with those of the anti-laminarin antibody ELISA. Higher titres were observed using the anti-laminarin antibody ELISA.

Immunogenicity Study (5)

In another study, conjugates prepared as described in Conjugation (2) and laminarin conjugated to CRM197 were combined with various individual and combined adjuvants and administered to mice by intrapertioneal administration. The laminarin conjugated to CRM197 was prepared as described in Immunogenicity study (1), except for an alternative lot of laminarin to CRM197 (lot 11AD) which was prepared without an amination step prior to conjugation.

CD2F1 mice, 4-6 weeks old, were tested in 11 groups of 16. The conjugates were used at a saccharide dose of 5 µg in a dosage volume of 150 µl, administered by intraperitoneal administration at days 1, 14 and 28. Blood samples were taken on days 0, 28 and 42 for assessing anti-laminarin antibody levels by ELISA.

Groups 1-3 received three identical doses of a) 17-mer-C2 β(1-3)-CRM conjugate; b) 15-mer-C6 β(1-3)-CRM conjugate; or c) 15-mer-C2 β(1-3)-CRM conjugate respectively, all with no adjuvant. Groups 4-6 received three identical doses of a) 17-mer-C2 β(1-3)-CRM conjugate; b) 15-mer-C6 β(1-3)-CRM conjugate; or c) 15-mer-C2 β(1-3)-CRM conjugate respectively, all with the MF59 oil-in-water emulsion adjuvant (75 µl). Groups 7-8 received three identical doses of laminarin conjugated to CRM197 with a) no adjuvant; or b) the MF59 oil-in-water emulsion adjuvant (75 µl) respectively. Groups 9-10 received three identical doses of laminarin conjugated to CRM197 with a) the MF59 oil-in-water emulsion adjuvant (75 µl) combined with IC31 at a high dose (49.5 µl of a sample having over 1000 nmol/ml oligodeoxynucleotide and 40 nmol/ml peptide); or b) an aluminium hydroxide adjuvant (300 µg), respectively. Group 11 received three identical doses of a different preparation of laminarin conjugated to CRM197 with the MF59 oil-in-water emulsion adjuvant (75 µl).

Figure 12:
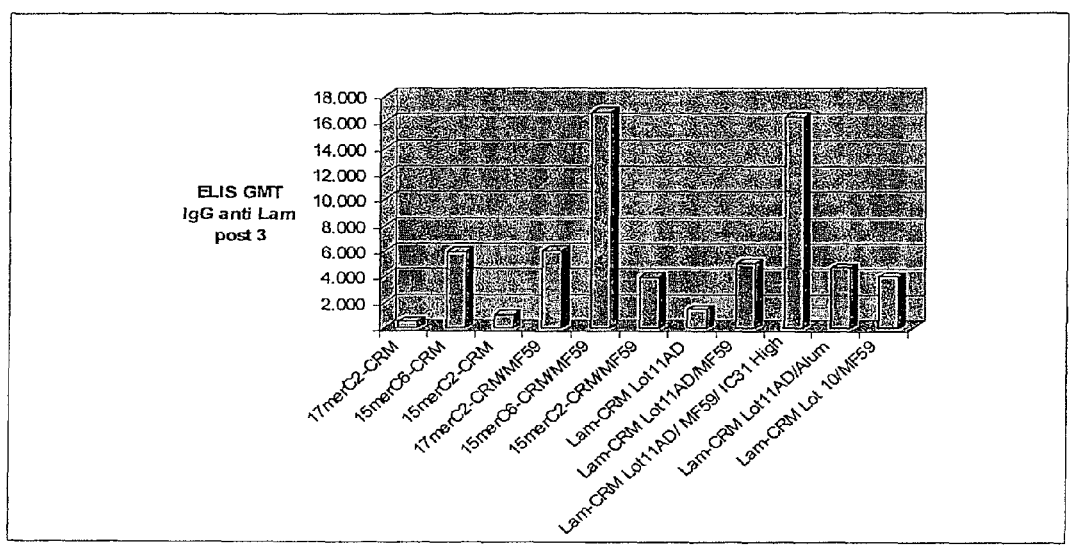
FIG. 12 shows IgG GMT (anti-laminarin) against synthetic glucan and laminarin conjugates alone or combined with various individual and combined adjuvants administered by intrapertioneal administration.

Anti-laminarin antibodies (GMT) at day 42 after administration of the conjugates are shown in FIG. 12. The results show that the synthetic curdlan and laminarin conjugates have similar immunogenicity as the other conjugates. When an adjuvant is present, the immunogenicity may be improved by using a synthetic version of the relevant glucan (compare the response seen after administration of 17-mer-C2 β(1-3)-CRM/MF59 (bar 4) with the response seen after administration of laminarin conjugated to CRM197/MF59 (bars 7 and 11)). The immunogenicity of the synthetic glucans may be improved by using a longer spacer between the glucan and the carrier protein (compare the response seen after administration of 15-mer-C6 β(1-3)-CRM and 15-mer-C6 β(1-3)-CRM/MF59 (bars 2 and 5) with the response seen after administration of 15-mer-C2 β(1-3)-CRM and 15-mer-C2 β(1-3)-CRM/MF59 (bars 3 and 6)). In the absence of adjuvant, immunogenicity to the synthetic glucans may be improved by the absence of β-1,6-branching (compare the response seen after administration of 15-mer-C2 β(1-3)-CRM (bar 3) with the response seen after administration of 17-mer-C2 β(1-3)-CRM (bar 1). In contrast, in the presence of adjuvant, immunogenicity to the synthetic glucans may be improved by the presence of β-1,6-branching (compare the response seen after administration of 17-mer-C2 β(1-3)-CRM/MF59 (bar 4) with the response seen after administration of 15-mer-C2 β(1-3)-CRM/MF59 (bar 6). For the laminarin conjugated to CRM197, the omission of an amination step prior to conjugation did not prevent immunogenicity (compare bars 8 and 11).

Active Protection Study (1)

In another study, the ability of mice receiving glucans conjugated to CRM197 combined with MF59 adjuvant to survive challenge with C. albicans was tested. The conjugates were prepared as described in Immunogenicity study (1).

Female, four-week old CD2F1 mice (Harlan) were immunized with three doses of laminarin or curdlan conjugated to CRM197, each dose consisting of 10 µg polysaccharide in 0.2 ml of PBS:MF59 (1:1 v/v) per mouse.

The immunization schedule was:
Day 0—first dose by subcutaneous administration
Day 14—second dose by intraperitoneal administration
Day 28—third dose by intraperitoneal administration
Day 35—bleeding
Day 40—fungal challenge by intravenous administration of $5.0 \times 10^5$ (after immunisation with the laminarin conjugate) or $2.5 \times 10^5$ (after immunisation with the curdlan conjugate) C. albicans strain BP cells in 0.2 ml PBS per mouse.

Protection endpoints were measured in terms of mortality (median survival time (MST) and ratio of dead/total challenged mice).

Figure 13:
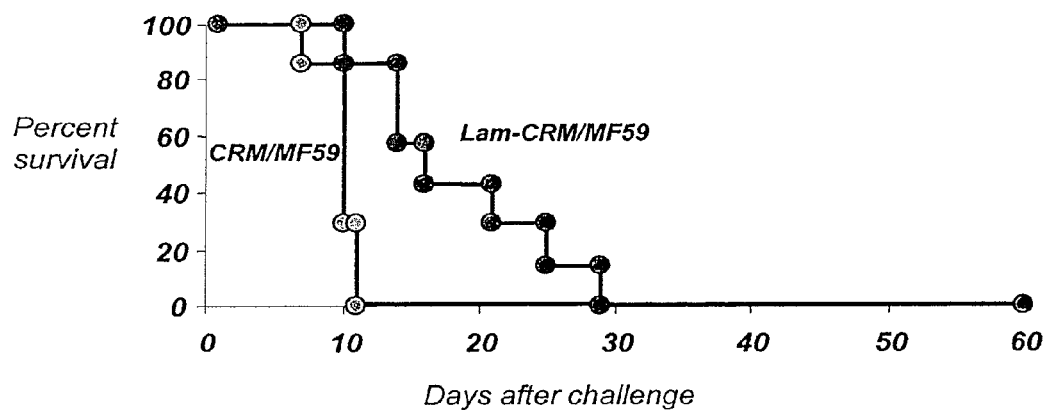
FIG. 13 shows the survival rate of mice treated with laminarin conjugated to CRM197 combined with MF59 or CRM197 and MF59 alone prior to challenge with *C. albicans*.

FIG. 13 shows the survival rate of mice treated with laminarin conjugated to CRM197 combined with MF59 or CRM197 and MF59 alone prior to challenge with C. albicans. The longer survival of mice treated with the conjugate is also shown in terms of MST in Table 3.

TABLE 3

| Vaccine | MST (days) |
| --- | --- |
| CRM197/MF59 | 10 |
| Lam-CRM197/MF59 | 16 |

Figure 14:
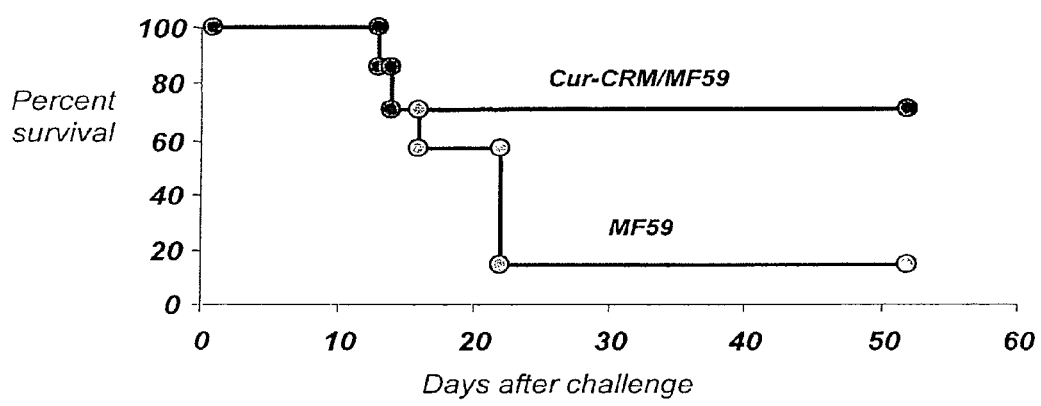
FIG. 14 shows the survival rate of mice treated with curdlan conjugated to CRM197 combined with MF59 or MF59 alone prior to challenge with *C. albicans*.

FIG. 14 shows the survival rate of mice treated with curdlan conjugated to CRM197 combined with MF59 or MF59 alone prior to challenge with C. albicans. The longer survival of mice treated with the conjugate is also shown in terms of MST in Table 4.

TABLE 4

| Vaccine | MST (days) |
| --- | --- |
| MF59 | 16 |
| Cur-CRM197/MF59 | >52 |

Survival was greater in mice receiving curdlan conjugated to CRM197 than in mice receiving laminarin conjugated to CRM197.

Active Protection Study (2)

In a similar study, the ability of mice receiving synthetic glucans conjugated to CRM197 combined with MF59 adjuvant to survive challenge with C. albicans was tested. The conjugates were prepared as described in Conjugation (2). In this study, fungal challenge was by intravenous administration of $5.0 \times 10^5$ cells.

Figure 15:
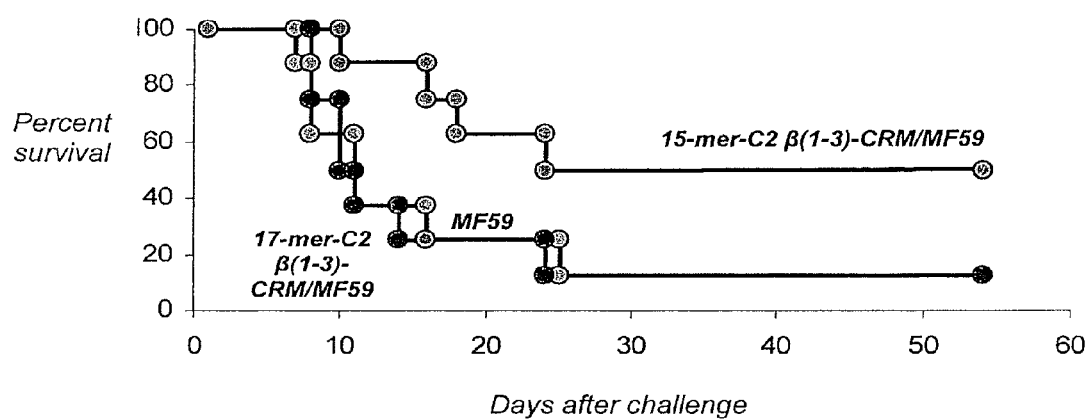
FIG. 15 shows the survival rate of mice treated with two synthetic glucan conjugates combined with MF59 or MF59 alone prior to challenge with *C. albicans*.

FIG. 15 shows the survival rate of mice treated with 15-mer-C2 β(1-3)-CRM combined with MF59, 17-mer-C2 β(1-3)-CRM combined with MF59 or MF59 alone prior to challenge with C. albicans. The longer survival of mice treated with the 15-mer-C2 β(1-3)-CRM conjugate is also shown in terms of MST in Table 5.

TABLE 5

| Vaccine | MST (days) |
| --- | --- |
| MF59 | 11 |
| 17mer-C2-CRM197/MF59 | 10 |
| 15mer-C2-CRM197/MF59 | 24 |

Treatment with 15-mer-C2 β(1-3)-CRM resulted in increased survival, while treatment with 17-mer-C2 β(1-3)-CRM did not seem to have any effect. This result suggests that the epitope responsible for inducing a protective antibody response in glucan comprises at least five adjacent non-terminal residues linked to other residues only by β-1,3 linkages. Without wishing to be bound by theory, it is though that this effect may contribute to the greater protective antibody response seen in mice receiving curdlan conjugated to CRM197 than in mice receiving laminarin conjugated to CRM197 in Active protection study (1). The curdlan conjugated to CRM197 (wherein the glucan comprises β-1,3-linked residues only) may contain a greater proportion of protective epitopes than the laminarin conjugated to CRM197 (wherein the glucan comprises β-1,3-linked residues and β-1,6-linked residues).

It will be understood that the invention has been described by way of example only and modifications may be made whilst remaining within the scope and spirit of the invention.

REFERENCES

[1] Deepe (1997) *Clin. Microbiol. Rev.* 10:585-596.
[2] Cassone & Torosantucci (2006) *Expert Rev Vaccines* 5:859-67.
[3] WO03/097091
[4] Torosantucci et al. (2005) *J Exp Med* 202:597-606.
[5] WO2006/030318.
[6] Pang et al. (2005) *Biosci Biotechnol Biochem* 69:553-8.
[7] U.S. Pat. No. 5,504,079.
[8] Takeo and Tei (1986) *Carbohydr Res.* 145:293-306
[9] Tanaka et al. (2003) *Tetrahedron Letters* 44:3053-3057
[10] Ning et al. (2002) *Tetrahedron Letters* 43:5545-5549
[11] Geurtsen et al. (1999) *Journal of Organic Chemistry* 64 (21):7828-7835
[12] Wu et al. (2003) *Carbohydr Res.* 338:2203-12
[13] Nicolaou et al. (1997). *J. Am. Chem. Soc.* 119:449-450
[14] Yamada et al. (1999) *Tetrahedron Letters* 40:4581-4584
[15] Yamago et al. (2001) *Org. Lett.* 24:3867-3870
[16] Yuguo et al. (2004) *Tetrahedron* 60: 6345-6351
[17] Amaya et al. (2001) *Tetrahedron Letters* 42:9191-9194
[18] Mei et al. (2005) *Carbohydr Res.* 340:2345-2351
[19] Takeo et al. (1993) *Carbohydr Res.* 245:81-96
[20] Jamois et al. (2005) *Glycobiology* 15(4):393-407
[21] Lefeber et al. (2001) *Chem. Eur. J.* 7(20):4411-4421
[22] Huang et al. (2005) *Carbohydr Res.* 340:603-608
[23] U.S. Pat. No. 5,508,191.
[24] MiKyoung et al. (2003) *Biochemical Engineering Journal*, 16:163-8.
[25] Barsanti et al. (2001) *J Appl Phycol* 13:59-65.
[26] Bardotti et al. (2008) *Vaccine* 26:2284-96
[27] Lindberg (1999) Vaccine 17 Suppl 2:S28-36
[28] Buttery & Moxon (2000) *J R Coll Physicians Lond* 34:163-8
[29] Ahmad & Chapnick (1999) *Infect Dis Clin North Am* 13:113-33, vii
[30] Goldblatt (1998) *J. Med. Microbiol.* 47:563-567
[31] EP-B-0 477 508
[32] U.S. Pat. No. 5,306,492
[33] WO98/42721
[34] Dick et al. in *Conjugate Vaccines* (eds. Cruse et al.) Karger, Basel, 1989, Vol. 10, 48-114
[35] Hermanson *Bioconjugate Techniques*, Academic Press, San Diego Calif. (1996)
[36] Ramsay et al. (2001) *Lancet* 357(9251):195-6
[37] Lees et al. (1996) *Vaccine* 14:190-198.
[38] WO95/08348.
[39] U.S. Pat. No. 4,761,283
[40] U.S. Pat. No. 4,356,170
[41] U.S. Pat. No. 4,882,317
[42] U.S. Pat. No. 4,695,624
[43] *Mol. Immunol.*, 1985, 22, 907-919
[44] EP-A-0208375
[45] Bethell G. S. et al., *J. Biol. Chem.*, 1979, 254, 2572-4
[46] Hearn M. T. W., *J. Chromatogr.*, 1981, 218, 509-18
[47] WO00/10599
[48] Gever et al., Med. Microbiol. Immunol, 165: 171-288 (1979).
[49] U.S. Pat. No. 4,057,685.
[50] U.S. Pat. Nos. 4,673,574; 4,761,283; 4,808,700.
[51] U.S. Pat. No. 4,459,286.
[52] U.S. Pat. No. 5,204,098
[53] U.S. Pat. No. 4,965,338
[54] U.S. Pat. No. 4,663,160.
[55] WO2007/000343.
[56] *Research Disclosure*, 453077 (January 2002)
[57] EP-A-0372501.
[58] EP-A-0378881.
[59] EP-A-0427347.
[60] WO93/17712
[61] WO94/03208.
[62] WO98/58668.
[63] EP-A-0471177.
[64] WO91/01146
[65] Falugi et al. (2001) *Eur J Immunol* 31:3816-3824.
[66] Baraldo et al. (2004) *Infect Immun* 72(8):4884-7.
[67] EP-A-0594610.
[68] Ruan et al. (1990) *J Immunol* 145:3379-3384.
[69] WO00/56360.
[70] Kuo et al. (1995) *Infect Immun* 63:2706-13.
[71] Michon et al. (1998) *Vaccine*. 16:1732-41.
[72] WO02/091998.
[73] WO01/72337
[74] WO00/61761.
[75] WO00/33882
[76] WO99/42130
[77] WO96/40242
[78] Lei et al. (2000) *Dev Biol* (Basel) 103:259-264
[79] WO00/38711
[80] Gennaro (2000) *Remington: The Science and Practice of Pharmacy*. 20th edition, ISBN: 0683306472.
[81] Almeida & Alpar (1996) *J. Drug Targeting* 3:455-467.
[82] U.S. Pat. No. 6,355,271.
[83] WO00/23105.
[84] U.S. Pat. No. 5,057,540.
[85] WO96/33739.
[86] EP-A-0109942.
[87] WO96/11711.
[88] WO00/07621.
[89] Barr et al. (1998) *Advanced Drug Delivery Reviews* 32:247-271.
[90] Sjolanderet et al. (1998) *Advanced Drug Delivery Reviews* 32:321-338.
[91] Pizza et al. (2000) *Int J Med Microbiol* 290:455-461.
[92] WO95/17211.
[93] WO98/42375.
[94] Singh et all (2001) *J Cont Release* 70:267-276.
[95] WO99/27960.
[96] U.S. Pat. No. 6,090,406
[97] U.S. Pat. No. 5,916,588
[98] EP-A-0626169.
[99] Dyakonova et al. (2004) Int Immunopharmacol 4(13): 1615-23.
[100] FR-2859633.
[101] Signorelli & Hadden (2003) *Int Immunopharmacol* 3(8):1177-86.
[102] WO2004/064715.
[103] De Libero et al, *Nature Reviews Immunology*, 2005, 5: 485-496

[104] U.S. Pat. No. 5,936,076.
[105] Oki et al, *J. Clin. Investig.*, 113: 1631-1640
[106] US2005/0192248
[107] Yang et al, *Angew. Chem. Int. Ed.*, 2004, 43: 3818-3822
[108] WO2005/102049
[109] Goff et al, *J. Am. Chem., Soc.*, 2004, 126: 13602-13603
[110] WO03/105769
[111] Cooper (1995) *Pharm Biotechnol* 6:559-80.
[112] Kandimalla et al. (2003) *Nucleic Acids Research* 31:2393-2400.
[113] WO02/26757.
[114] WO99/62923.
[115] Krieg (2003) *Nature Medicine* 9:831-835.
[116] McCluskie et al. (2002) *FEMS Immunology and Medical Microbiology* 32:179-185.
[117] WO98/40100.
[118] U.S. Pat. No. 6,207,646.
[119] U.S. Pat. No. 6,239,116.
[120] U.S. Pat. No. 6,429,199.
[121] Kandimalla et al. (2003) *Biochemical Society Transactions* 31 (part 3):654-658.
[122] Blackwell et al. (2003) *J Immunol* 170:4061-4068.
[123] Krieg (2002) *Trends Immunol* 23:64-65.
[124] WO01/95935.
[125] Kandimalla et al. (2003) *BBRC* 306:948-953.
[126] Bhagat et al. (2003) *BBRC* 300:853-861.
[127] WO03/035836.
[128] WO01/22972.
[129] Schellack et al. (2006) *Vaccine* 24:5461-72.
[130] Myers et al. (1990) pages 145-156 of *Cellular and molecular aspects of endotoxin reactions*.
[131] Ulrich (2000) Chapter 16 (pages 273-282) of reference 167.
[132] Johnson et al. (1999) *J Med Chem* 42:4640-9.
[133] Baldrick et al. (2002) *Regulatory Toxicol Pharmacol* 35:398-413.
[134] WO 94/21292.
[135] U.S. Pat. No. 4,680,338.
[136] U.S. Pat. No. 4,988,815.
[137] WO92/15582.
[138] Stanley (2002) *Clin Exp Dermatol* 27:571-577.
[139] Wu et al. (2004) *Antiviral Res.* 64(2):79-83.
[140] Vasilakos et al. (2000) *Cell Immunol.* 204(1):64-74.
[141] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[142] Jones (2003) *Curr Opin Investig Drugs* 4:214-218.
[143] WO2004/060308.
[144] WO2004/064759.
[145] U.S. Pat. No. 6,924,271.
[146] US2005/0070556.
[147] U.S. Pat. No. 5,658,731.
[148] U.S. Pat. No. 5,011,828.
[149] WO2004/87153.
[150] U.S. Pat. No. 6,605,617.
[151] WO02/18383.
[152] WO2004/018455.
[153] WO03/082272.
[154] Johnson et al. (1999) *Bioorg Med Chem Lett* 9:2273-2278.
[155] Evans et al. (2003) *Expert Rev Vaccines* 2:219-229.
[156] Andrianov et al. (1998) *Biomaterials* 19:109-115.
[157] Payne et al. (1998) *Adv Drug Delivery Review* 31:185-196.
[158] WO03/011223.
[159] Meraldi et al. (2003) *Vaccine* 21:2485-2491.
[160] Pajak et al. (2003) *Vaccine* 21:836-842.
[161] Wong et al. (2003) *J Clin Pharmacol* 43(7):735-42.
[162] US2005/0215517.
[163] WO90/14837.
[164] Podda & Del Giudice (2003) *Expert Rev Vaccines* 2:197-203.
[165] Podda (2001) *Vaccine* 19: 2673-2680.
[166] *Vaccine Design: The Subunit and Adjuvant Approach* (eds. Powell & Newman) Plenum Press 1995 (ISBN 0-306-44867-X).
[167] *Vaccine Adjuvants: Preparation Methods and Research Protocols* (Volume 42 of *Methods in Molecular Medicine* series). ISBN: 1-59259-083-7. Ed. O'Hagan.
[168] Allison & Byars (1992) *Res Immunol* 143:519-25.
[169] Hariharan et al. (1995) *Cancer Res* 55:3486-9.
[170] WO95/11700.
[171] U.S. Pat. No. 6,080,725.
[172] WO2005/097181.
[173] Wills et al. (2000) *Emerging Therapeutic Targets* 4:1-32.
[174] WO03/097091
[175] Torosantucci et al. (2005) *J Exp Med* 202:597-606
[176] WO03/009869.

---

The invention claimed is:

1. A method of raising a protective antibody response in a mammal comprising administering to the mammal an immunogenic conjugate comprising a glucan covalently linked to a bacterial toxin or CRM197 carrier thereby providing the protective antibody response which is specific for the glucan, wherein the protective antibody response is capable of protecting against infections of *Candida* species in the mammal, and wherein the glucan has exclusively linear β-1,3-linked glucose residues, wherein the glucan comprises one or more sequences of at least five adjacent non-terminal glucose residues linked to other glucose residues only by β-1,3-linkages.

2. The method of claim 1, wherein the glucan is linear β-D-glucopyranose with exclusively 1,3 linkages.

3. The method of claim 1, wherein the glucan is a curdlan, a paramylon, or a fragment thereof.

4. The method of claim 3, wherein the glucan is a hydrolysis fragment of the curdlan.

5. The method of claim 1, wherein the glucan has the following structure:

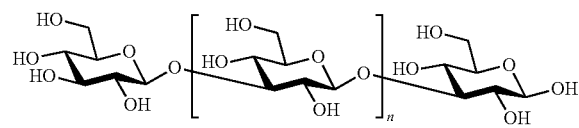

wherein n+2 is in the range of 11-19.

6. The method of claim 5, wherein the n+2 is 15.

7. The method of claim 1, wherein the glucan is covalently linked to the carrier directly.

8. The method of claim 1, wherein the glucan is covalently linked to the carrier via a linker.

9. The method of claim 1, wherein the conjugate is comprised in a pharmaceutical composition in combination with a pharmaceutically acceptable carrier.

10. The method of claim 9, wherein the composition is an immunogenic composition.

11. The method of claim 10, wherein the composition includes an adjuvant.

12. The method of claim 5, wherein the conjugate is comprised in a pharmaceutical composition in combination with a pharmaceutically acceptable carrier.

13. The method of claim 12, wherein the composition comprises an adjuvant.

14. The method of claim 13, wherein the adjuvant is a CpG oligodeoxynucleotide, MF59, LT-K63, α-galactosylceramide or aluminum salt.

* * * * *